(12) United States Patent
Lee et al.

(10) Patent No.: US 9,234,035 B2
(45) Date of Patent: Jan. 12, 2016

(54) ANTIBODIES TO INTERLEUKIN-6

(71) Applicant: Fountain Biopharma Inc., Taipei (TW)

(72) Inventors: Tong-Young Lee, Taipei (TW);
Han-Chung Wu, Taipei (TW); Tanny Chen Tsao, Taipei (TW); Willie Lin, Taipei (TW)

(73) Assignee: Fountain Biopharma Inc., Taipei (TW)

( * ) Notice: Subject to any disclaimer, the term of this patent is extended or adjusted under 35 U.S.C. 154(b) by 216 days.

(21) Appl. No.: 14/057,349

(22) Filed: Oct. 18, 2013

(65) Prior Publication Data

US 2014/0112935 A1    Apr. 24, 2014

Related U.S. Application Data

(60) Provisional application No. 61/716,802, filed on Oct. 22, 2012.

(51) Int. Cl.
| | |
|---|---|
| *C07K 16/24* | (2006.01) |
| *A61K 39/395* | (2006.01) |
| *A61K 31/282* | (2006.01) |
| *A61K 31/337* | (2006.01) |
| *A61K 31/7068* | (2006.01) |
| *A61K 45/06* | (2006.01) |
| *A61K 39/00* | (2006.01) |

(52) U.S. Cl.
CPC ............. *C07K 16/248* (2013.01); *A61K 31/282* (2013.01); *A61K 31/337* (2013.01); *A61K 31/7068* (2013.01); *A61K 39/3955* (2013.01); *A61K 45/06* (2013.01); *A61K 2039/505* (2013.01); *C07K 2317/21* (2013.01); *C07K 2317/73* (2013.01); *C07K 2317/76* (2013.01); *C07K 2317/92* (2013.01)

(58) Field of Classification Search
CPC ............... C07K 16/24; C07K 2317/21; A61K 2039/505
See application file for complete search history.

(56) References Cited

FOREIGN PATENT DOCUMENTS

| EP | 1 536 012 A1 | 6/2005 |
|---|---|---|
| WO | WO 2004/039826 A1 | 5/2004 |
| WO | WO 2006/119115 A2 | 11/2006 |
| WO | WO 2006/121168 A1 | 11/2006 |
| WO | WO 2007/066082 A1 | 6/2007 |
| WO | WO 2008/019061 A2 | 2/2008 |
| WO | WO 2008/065378 A2 | 6/2008 |
| WO | WO 2009/155180 A1 | 12/2009 |
| WO | WO 2010/056948 A2 | 5/2010 |
| WO | WO 2010/088444 A1 | 8/2010 |
| WO | WO 2011/079308 A2 | 6/2011 |
| WO | WO 2012/092374 A2 | 7/2012 |

OTHER PUBLICATIONS

Genbank Submission; NCBI, Accession No. BAC01886.1; Akahori et al.; Jul. 2, 2002.
Genbank Submission; NCBI, Accession No. BAC02221.1; Akahori et al.; Jul. 2, 2002.
Genbank Submission; NCBI, Accession No. BAC02265.1; Akahori et al.; Jul. 2, 2002.
Carter, Potent antibody therapeutics by design. Nat Rev Immunol. May 2006;6(5):343-57.
Davies et al., Affinity improvement of single antibody VH domains: residues in all three hypervariable regions affect antigen binding. Immunotechnology. Sep. 1996;2(3):169-79.
Holt et al., Domain antibodies: proteins for therapy. Trends Biotechnol. Nov. 2003;21(11):484-90.
Wark et al., Latest technologies for the enhancement of antibody affinity. Adv Drug Deliv Rev. Aug. 7, 2006;58(5-6):657-70. Epub May 22, 2006.

*Primary Examiner* — Prema Mertz
(74) *Attorney, Agent, or Firm* — Wolf, Greenfield & Sacks, P.C.

(57) ABSTRACT

The present disclosure provides antibodies that bind to human interleukin-6 (IL6). The antibodies can modulate IL6 signaling and thus used in treatment or prevention of IL6 associated diseases or disorders, particularly inflammatory disorder, rheumatoid arthritis (RA), angiogenesis, and cancer.

15 Claims, 26 Drawing Sheets

A

B

C

|  |  | IC$_{50}$ (µg/ml) |
|---|---|---|
| ○ | Plot#1 1-4-62 | 0.618 |
| □ | Plot#2 Ag1-4-6 | 0.0468 |
| △ | Plot#3 HAg1T-3-10 | 0.00456 |
| ◇ | Plot#4 hIgG1 |  |

A

**, $P < 0.01$

B

C

F

A

C

F

**, P < 0.01

G

B

A

SEQUENCE LISTING

<160> NUMBER OF SEQ ID NOS: 21

<210> SEQ ID NO 1
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 1

Glu Val Gln Leu Val Glu Ser Gly Pro Ala Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 2
<211> LENGTH: 7
<212> TYPE: PRT

<213> ORGANISM: Artificial Sequence
<220> FEATURE:
<223> OTHER INFORMATION: Synthetic polypeptide

<400> SEQUENCE: 2

Thr Gly Gly Met Ser Val Ser
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 3

Trp Ile Arg Gln Pro Pro Gly Lys Ala Leu Glu Trp Leu Ala
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 4

Arg Ile Asp Trp Asp Asp Asp Lys Phe Tyr Thr Pro Ser Leu Lys Thr
1               5                   10                  15

<210> SEQ ID NO 5
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 5

Arg Leu Thr Ile Ser Arg Asp Thr Ser Lys Asn Gln Val Val Leu Ile
1               5                   10                  15

Met Thr Asn Met Asp Pro Val Asp Thr Ala Thr Tyr Tyr Cys Ala Arg
            20                  25                  30

<210> SEQ ID NO 6
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 6

Met His Ile Asp Asp Ser Asn Gly Tyr Tyr Ser Asp Ala Phe His Ile
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 7

Trp Gly Gln Gly Thr Met Val Thr Val Ser Ser
1               5                   10

<210> SEQ ID NO 8

```
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 8

Glu Ile Val Leu Thr Gln Ser Pro Ala Thr Leu Ser Val Ser Pro Gly
1               5                   10                  15

Glu Arg Val Thr Leu Ser Cys
            20

<210> SEQ ID NO 9
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 9

Arg Asp Ser Gln Ser Val Ser Ser Thr Ser Leu Ala
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 10

Trp Tyr Gln Gln Lys Ser Gly Gln Ala Pro Arg Leu Leu Ile Tyr
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 11

Asp Thr Ser Asn Arg Ala Thr
1               5

<210> SEQ ID NO 12
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 12

Gly Ile Pro Ala Arg Phe Ser Gly Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 13
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 13
```

```
Leu Val Arg Asn Asn Trp Pro Pro Arg Phe Thr
 1               5                  10
```

<210> SEQ ID NO 14
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 14

```
Phe Gly Gln Gly Thr Lys Val Glu Ile Lys
 1               5                  10
```

<210> SEQ ID NO 15
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 15

```
Ser Phe Val Ser Arg Pro Tyr Pro Arg Phe Thr
 1               5                  10
```

<210> SEQ ID NO 16
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 16

```
Met His Ile Asp Asp Ser Asn Gly Tyr Phe Ser Asp Ala Phe His Ile
 1               5                  10                  15
```

<210> SEQ ID NO 17
<211> LENGTH: 126
<212> TYPE: PRT
<213> ORGANISM: Artificial Sequence
<220> FEATURE:
<223> OTHER INFORMATION: Synthetic polypeptide

<400> SEQUENCE: 17

```
Glu Val Gln Leu Val Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Gly
                20                  25                  30

Gly Met Ser Val Ser Trp Ile Arg Gln Pro Pro Gly Lys Ala Leu Glu
            35                  40                  45

Trp Leu Ala Arg Ile Asp Trp Asp Asp Lys Phe Tyr Thr Pro Ser
     50                  55                  60

Leu Lys Thr Arg Leu Thr Ile Ser Arg Asp Thr Ser Lys Asn Gln Val
 65                  70                  75                  80

Val Leu Ile Met Thr Asn Met Asp Pro Val Asp Thr Ala Thr Tyr Tyr
                 85                  90                  95

Cys Ala Arg Met His Ile Asp Asp Ser Asn Gly Tyr Tyr Ser Asp Ala
            100                 105                 110

Phe His Ile Trp Gly Gln Gly Thr Met Val Thr Val Ser Ser
        115                 120                 125
```

<210> SEQ ID NO 18
<211> LENGTH: 126

<212> TYPE: PRT
<213> ORGANISM: Artificial Sequence
<220> FEATURE:
<223> OTHER INFORMATION: Synthetic polypeptide

<400> SEQUENCE: 18

```
Glu Val Gln Leu Val Glu Ser Gly Pro Ala Leu Val Lys Pro Thr Gln
1               5                   10                  15

Thr Leu Thr Leu Thr Cys Thr Phe Ser Gly Phe Ser Leu Ser Thr Gly
            20                  25                  30

Gly Met Ser Val Ser Trp Ile Arg Gln Pro Pro Gly Lys Ala Leu Glu
        35                  40                  45

Trp Leu Ala Arg Ile Asp Trp Asp Asp Asp Lys Phe Tyr Thr Pro Ser
    50                  55                  60

Leu Lys Thr Arg Leu Thr Ile Ser Arg Asp Thr Ser Lys Asn Gln Val
65                  70                  75                  80

Val Leu Ile Met Thr Asn Met Asp Pro Val Asp Thr Ala Thr Tyr Tyr
                85                  90                  95

Cys Ala Arg Met His Ile Asp Asp Ser Asn Gly Tyr Phe Ser Asp Ala
            100                 105                 110

Phe His Ile Trp Gly Gln Gly Thr Met Val Thr Val Ser Ser
            115                 120                 125
```

<210> SEQ ID NO 19
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 19

```
Glu Ile Val Leu Thr Gln Ser Pro Ala Thr Leu Ser Val Ser Pro Gly
1               5                   10                  15

Glu Arg Val Thr Leu Ser Cys Arg Asp Ser Gln Ser Val Ser Ser Thr
            20                  25                  30

Ser Leu Ala Trp Tyr Gln Gln Lys Ser Gly Gln Ala Pro Arg Leu Leu
        35                  40                  45

Ile Tyr Asp Thr Ser Asn Arg Ala Thr Gly Ile Pro Ala Arg Phe Ser
    50                  55                  60

Gly Gly Gly Ser Gly Thr Asp Phe Thr Leu Thr Ile Ser Ser Leu Glu
65                  70                  75                  80

Pro Glu Asp Phe Ala Val Tyr Tyr Cys Leu Val Arg Asn Asn Trp Pro
                85                  90                  95

Pro Arg Phe Thr Phe Gly Gln Gly Thr Lys Val Glu Ile Lys
            100                 105                 110
```

<210> SEQ ID NO 20
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 20

```
Glu Ile Val Leu Thr Gln Ser Pro Ala Thr Leu Ser Val Ser Pro Gly
1               5                   10                  15

Glu Arg Val Thr Leu Ser Cys Arg Asp Ser Gln Ser Val Ser Ser Thr
            20                  25                  30

Ser Leu Ala Trp Tyr Gln Gln Lys Ser Gly Gln Ala Pro Arg Leu Leu
```

```
                    35                  40                  45
Ile Tyr Asp Thr Ser Asn Arg Ala Thr Gly Ile Pro Ala Arg Phe Ser
        50                  55                  60

Gly Gly Gly Ser Gly Thr Asp Phe Thr Leu Thr Ile Ser Ser Leu Glu
65                  70                  75                  80

Pro Glu Asp Phe Ala Val Tyr Tyr Cys Ser Phe Val Ser Arg Pro Tyr
                85                  90                  95

Pro Arg Phe Thr Phe Gly Gln Gly Thr Lys Val Glu Ile Lys
                100                 105                 110

<210> SEQ ID NO 21
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (10)..(10)
<223> OTHER INFORMATION: Xaa is an aromatic amino acid

<400> SEQUENCE: 21

Met His Ile Asp Asp Ser Asn Gly Tyr Xaa Ser Asp Ala Phe
1               5                   10
```

ANTIBODIES TO INTERLEUKIN-6

RELATED APPLICATIONS

This application claims the benefit of U.S. provisional application No. 61/716,802, filed Oct. 22, 2012 under 35 U.S.C. §119, the entire content of which is incorporated herein by reference.

BACKGROUND OF THE INVENTION

Human interleukin-6 (IL6), a secreted glycoprotein having 184 amino acids (21 kDa), has a four-helix bundle structure. IL6 is a multi-functional cytokine that acts on various type of cells, e.g., B cells, T cells, fibroblasts, hepatocytes, osteoclasts, neural cells, mesangial cells, epidermal keratinocytes, and hematopoietic progenitor cells, via binding to two distinct receptor proteins, the IL6 receptor (IL6R) and glycoprotein 130 (gp130). Formation of the IL6/IL6R/gp130 complex transduces intracellular signaling pathways, including those mediated by (1) phosphatidyl inositol-3'-kinase (PI3K), (2) mitogen-activated protein kinase (MAK), and (3) Janus tyrosine kinase (JAK)-signal transducer and activator of transcription 1 and 3 (STAT1 and STAT3).

IL6 functions as an immune regulator, cell growth factor, bone metabolism regulator, cell differentiation factor, and acute phase protein inducer against several effecter cells. In liver, IL6 induces various acute-phase proteins such as serum amyloid A (SAA), C-reactive protein (CRP), hepcidin, fibrinogen, and haptoglobin antichymotrypsin. The pathological significance of IL6 for various diseases has been indicated in numerous studies, including chronic inflammatory diseases, autoimmune diseases (e.g., rheumatoid arthritis, Crohn's disease, Castleman's disease and psoriasis), cancer (e.g., multiple myeloma, leukemia, breast cancer, pancreatic cancer, prostate cancer and various cancers), and cachexia and coronary heart disease.

It is therefore of great interest to develop new IL6 antagonists for use in treating diseases associated with the IL6 signaling.

SUMMARY OF THE INVENTION

The present disclosure is based on the identification of a number of exemplary anti-IL6 antibodies, e.g., 1-4-62, Ag1-4-6 (also known as FB704), or HAg1T-3-10, which unexpectedly showed high binding affinity and specificity to human IL6, and superior activities in inhibiting IL6-induced cell proliferation (e.g., cancer cell proliferation) and cytokine production (e.g., inflammatory cytokine production), angiogenesis, cancer-induced cachexia, and cancer metastasis. Such antibodies also significantly enhanced anti-cancer effects of other chemotherapeutic agents such as oxaliplatin, gemcitabine, and docetaxel.

Accordingly, one aspect of the present disclosure relates to an isolated antibody that binds to human interleukin 6 (IL6), comprising:

(a) a heavy chain variable region ($V_H$), which comprises a heavy chain complementary determining region 1 (HC CDR1) of SEQ ID NO: 2, a heavy chain complementary determining region 2 (HC CDR2) of SEQ ID NO: 4, and a heavy chain complementary determining region 3 (HC CDR3) of SEQ ID NO: 6 or SEQ ID NO: 16; or (b) a light chain variable region ($V_L$), which comprises a light chain complementary determining region 1 (LC CDR)1 of SEQ ID NO: 9, a light chain complementary determining region 2 (LC CDR2) of SEQ ID NO: 11, and a light chain complementary determining region 3 (LC CDR3) of SEQ ID NO: 13 or SEQ ID NO: 15.

In some embodiments, the isolated anti-IL6 antibody comprises (i) a $V_H$ that comprises the HC CDR1 of SEQ ID NO: 2, the HC CDR2 of SEQ ID NO: 4, and the HC CDR3 of SEQ ID NO: 6; or (ii) a $V_H$ that comprises the HC CDR1 of SEQ ID NO: 2, the HC CDR2 of SEQ ID NO: 4, and the HC CDR3 of SEQ ID NO: 16. In one example, the antibody comprises a $V_H$ that comprises the amino acid sequence of SEQ ID NO:17 or SEQ ID NO:18.

In other embodiments, the isolated anti-IL6 antibody further comprises (i) a $V_L$ that comprises the LC CDR1 of SEQ ID NO: 9, the LC CDR2 of SEQ ID NO: 11, and the LC CDR3 of SEQ ID NO: 13; or (ii) a $V_L$ that comprises the LC CDR1 of SEQ ID NO: 9, the LC CDR2 of SEQ ID NO: 11, and the LC CDR3 of SEQ ID NO: 15. In one example, the antibody further comprises a $V_L$ that comprises the amino acid sequence of SEQ ID NO:19 or SEQ ID NO:20.

Examples of the anti-IL6 antibodies as described here include, but are not limited to:

(i) an antibody comprising a $V_H$ that comprises the HC CDR1 of SEQ ID NO: 2, the HC CDR2 of SEQ ID NO: 4, and the HC CDR3 of SEQ ID NO: 6; and a $V_L$ that comprises the LC CDR1 of SEQ ID NO: 9, the LC CDR2 of SEQ ID NO: 11, and the CDR3 of SEQ ID NO: 13;

(ii) an antibody comprising a $V_H$ that comprises the HC CDR1 of SEQ ID NO: 2, the HC CDR2 of SEQ ID NO: 4, and the HC CDR3 of SEQ ID NO: 16, and a $V_L$ that comprises the LC CDR1 of SEQ ID NO: 9, the LC CDR2 of SEQ ID NO: 11, and the CDR3 of SEQ ID NO: 13;

(iii) an antibody comprising a $V_H$ that comprises the HC CDR1 of SEQ ID NO: 2, the HC CDR2 of SEQ ID NO: 4, and the HC CDR3 of SEQ ID NO: 6, and a $V_L$ that comprises the LC CDR1 of SEQ ID NO: 9, the LC CDR2 of SEQ ID NO: 11, and the CDR3 of SEQ ID NO: 15;

(iv) an antibody comprising a $V_H$ that comprises the HC CDR1 of SEQ ID NO: 2, the HC CDR2 of SEQ ID NO: 4, and the HC CDR3 of SEQ ID NO: 16, and a $V_L$ that comprises the LC CDR1 of SEQ ID NO: 9, the LC CDR2 of SEQ ID NO: 11, and the CDR3 of SEQ ID NO: 15;

(v) an antibody comprising a $V_H$ that comprises the amino acid sequence of SEQ ID NO: 17 and a $V_L$ that comprises the amino acid sequence of SEQ ID NO:19;

(vi) an antibody comprising a $V_H$ that comprises the amino acid sequence of SEQ ID NO: 17 and a $V_L$ that comprises the amino acid sequence of SEQ ID NO:20; and (vii) an antibody comprising a $V_H$ that comprises the amino acid sequence of SEQ ID NO: 18 and a $V_L$ that comprises the amino acid sequence of SEQ ID NO:19; and (viii) an antibody comprising a $V_H$ that comprises the amino acid sequence of SEQ ID NO: 18 and a $V_L$ that comprises the amino acid sequence of SEQ ID NO:20.

Any of the anti-IL6 antibodies described herein can be a full-length antibody or an antigen-binding fragment thereof, which can be Fab or $(Fab')_2$. Alternatively, the anti-IL6 antibody can be a single chain antibody, a humanized antibody, or a human antibody.

In another aspect, the present disclosure provides a nucleic acid comprising a nucleotide sequence encoding an antibody heavy chain variable region ($V_H$), an antibody light chain variable region ($V_L$) or both, wherein the $V_H$ and $V_L$ are as described herein.

In another aspect, the present disclosure provides a vector (e.g., an expression vector) comprising any of the nucleic acids described herein and a host cell comprising such a vector.

In yet another aspect, the present disclosure provides a method for producing an antibody that binds to human IL6, comprising: (i) culturing the host cell as described herein under conditions allowing for expression of the antibody, and optionally, (ii) harvesting the antibody.

Another aspect of the present disclosure relates to a composition (e.g., a pharmaceutical composition) comprising (a) any of the anti-IL6 antibody described herein, any of the nucleic acids described herein, or any of the vectors described herein; and (b) a carrier such as a pharmaceutically acceptable carrier.

In some embodiments, any of the compositions described herein further comprises another anti-cancer agent or a disease modifying antirheumatic drug (DMARD). Examples of the anti-cancer agent include, but are not limited to, docetaxel, oxaliplatin, and gemcitabine. Examples of DMARDs include, but are not limited to, methotrexate, azathioprine, chloroquine hydroxychloroquine, cyclosporin A, and sulfasalazine.

In yet another aspect, the present disclosure provides a method for treating a disease associated with IL6, comprising administering to a subject in need thereof a therapeutically effective amount of any of the anti-IL6 antibodies described herein, or any of the nucleic acids that encode such anti-IL6 antibodies. Examples of the disease associated with IL6 include, but are not limited to, inflammatory disorder, autoimmune diseases, angiogenesis, and cancer.

In some embodiments, the disease associated with IL6 is cancer, which can be multiple myeloma, leukemia, breast cancer, pancreatic cancer, lung cancer, ovarian cancer, oral cancer and prostate cancer. In some examples, the amount of the antibody or the encoding nucleic acid is effective in reducing tumor metastasis or cancer related cachexia. In other examples, the method further comprises administering to the subject another anti-cancer agent, e.g., oxaliplatin, gemcitabine, or docetaxel.

In other embodiments, the disease associated with IL6 is an autoimmune disease, e.g., rheumatoid arthritis (RA), Crohn's disease, Castleman's disease, multiple sclerosis, ankylosing spondylitis, psoriatic arthritis, or psoriasis. In some examples, the method described herein further comprises administering to the subject one or more disease modifying antirheumatic drugs (DMARDs), e.g., methotrexate, azathioprine, chloroquine, hydroxychloroquine, cyclosporin A, sulfasalazine.

Also within the scope of the present disclosure are pharmaceutical compositions for use in treating a disease associated with IL6, wherein the pharmaceutical composition comprises (a) any of the anti-IL6 antibodies or any of the nucleic acids/vectors described herein; (b) a pharmaceutically acceptable carrier; and optionally, (c) an anti-cancer agent or a DMARD as those described herein. Exemplary diseases associated with IL6 include, but are not limited to, inflammatory disorder, autoimmune diseases (e.g. rheumatoid arthritis (RA), Crohn's disease, Castleman's disease, multiple sclerosis, ankylosing spondylitis, psoriatic arthritis and psoriasis), angiogenesis, cancer (e.g. multiple myeloma, leukemia, breast cancer, pancreatic cancer, lung cancer, ovarian cancer, oral cancer and prostate cancer), tumor metastasis, cancer related cachexia.

Further, the present disclosure provides uses of any of the anti-IL6 antibodies or any of the encoding nucleic acids in medicament, or for use in the manufacture of a medicament for treating a disease or condition associated with IL6 as those described herein.

The details of one or more embodiments of the invention are set forth in the description below. Other features or advantages of the present invention will be apparent from the following drawings and detailed description of several embodiments, and also from the appended claims.

DETAILED DESCRIPTION OF THE INVENTION

Figure 1:
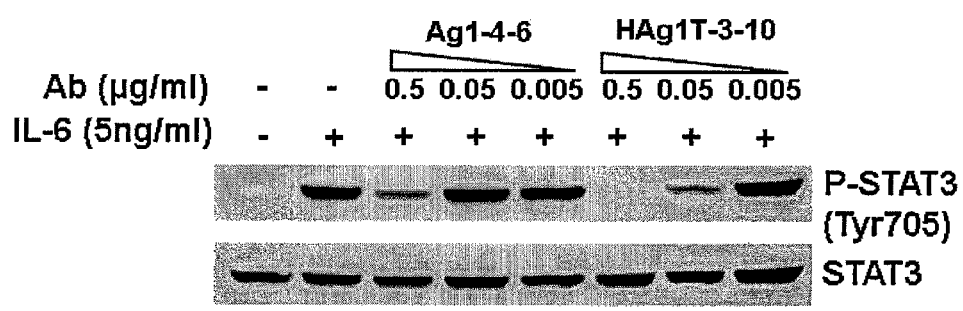
FIG. 1 is a diagram showing the efficacy of high-affinity anti-IL6 antibodies on cell signaling transduction pathway and proliferation. (A) phosphorylated-STAT3 signaling was decreased by anti-IL6 antibodies Ag1-4-6 and HAgT1-3-10 in a dose-dependent manner. (B) Anti-IL6 antibodies Ag1-4-6 and HAgT1-3-10 suppressed the STAT3 signaling at a much greater level as compared to control antibody Actemra. (C) Anti-IL6 antibodies 1-4-62, Ag1-4-6 and HAg1T-3-10 inhibited B9 cell proliferation in a dose-dependent manner and the $IC_{50}$ was 0.618, 0.0468 and 0.00456 µg/ml respectively.
Figure 1:
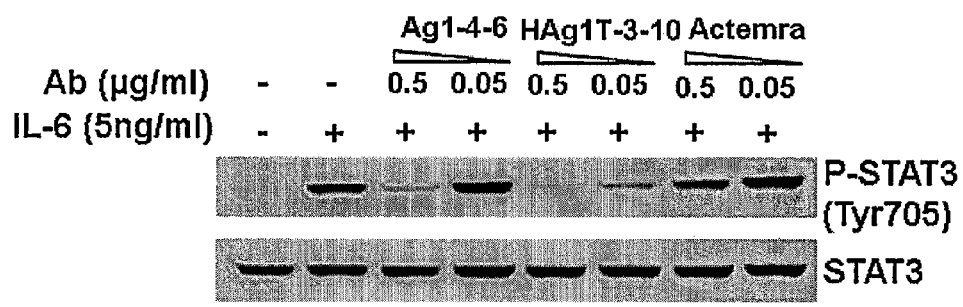
Figure 1:
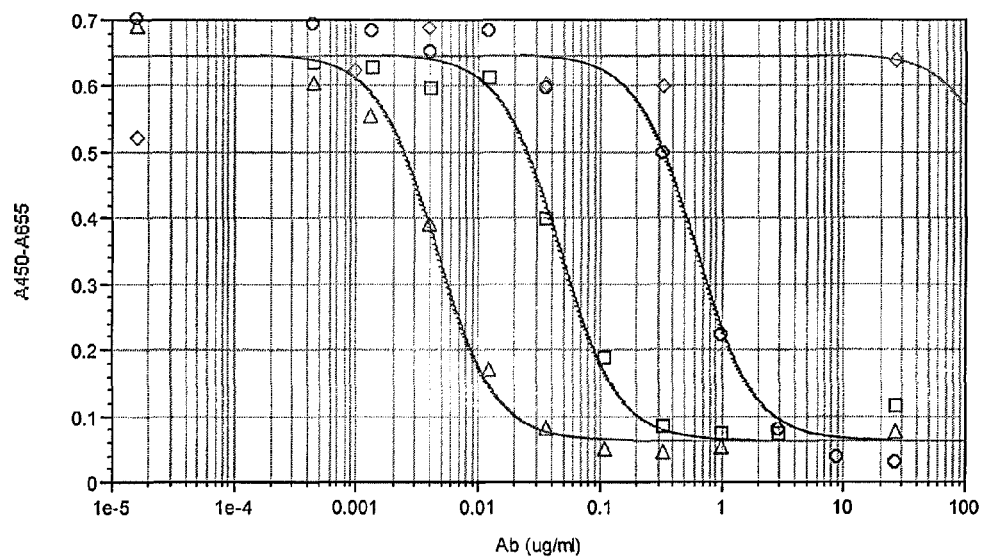

The present disclosure relates to antibodies that bind human interleukin-6 (IL6), which may neutralize IL6 activity, and their uses in regulating IL6-mediated signaling pathways. The anti-IL6 antibodies described herein are useful in the treatment of IL6 associated diseases or disorders, such as inflammatory disorders, autoimmune diseases, angiogenesis, cancer, tumor metastasis and cancer related cachexia.

The following description is merely intended to illustrate various embodiments of the invention. As such, specific embodiments discussed herein are not to be construed as limitations to the scope of the invention. It will be apparent to one skilled in the art that various changes or equivalents may be made without departing from the scope of the invention.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

DEFINITIONS

In order to provide a clear and ready understanding of the present disclosure, certain terms are first defined. Additional definitions are set forth throughout the detailed description. Unless defined otherwise, all technical and scientific terms used herein have the same meanings as is commonly understood by one of skill in the pertinent art.

As used herein, the articles "a" and "an" refer to one or more than one (i.e., at least one) of the grammatical object of the article. By way of example, "an element" means one element or more than one element.

As used herein, the term "polypeptide" refers to a polymer composed of amino acid residues linked via peptide bonds. The term "protein" typically refers to relatively large polypeptides. The term "peptide" typically refers to relatively short polypeptides (e.g., containing up to 100, 80, 60, 50, 30, or 20 amino acid residues).

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv)), mutants thereof, fusion proteins comprising an antibody portion, humanized antibodies, chimeric antibodies, diabodies, linear antibodies, single chain antibodies, multi-specific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies.

An intact or full-length antibody comprises two heavy chains and two light chains. Each heavy chain contains a heavy chain variable region ($V_H$) and a first, second and third constant regions ($C_H 1$, $C_H 2$ and $C_H 3$). Each light chain contains a light chain variable region ($V_L$) and a constant region (CL). A full-length antibody can be an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The term "antigen-binding domain" or "antigen-binding fragment" refers to a portion or region of an intact antibody molecule that is responsible for antigen binding. An antigen-binding domain may comprise the heavy chain variable region ($V_H$), the light chain variable region ($V_L$), or both. Each of the $V_H$ and $V_L$ typically contains three complementarity determining regions CDR1, CDR2, and CDR3. The three CDRs in the $V_H$ or $V_L$ are franked by framework regions (FR1, FR2, FR3, and FR4).

Examples of antigen-binding fragments of include, but are not limited to: (1) an Fab fragment, which can be a monovalent fragment having a $V_L$-$C_L$ chain and a $V_H$-$C_H$1 chain; (2) an F(ab')$_2$ fragment, which can be a bivalent fragment having two Fab fragments linked by a disulfide bridge at the hinge region, i.e. a dimer of Fab; (3) an Fv fragment having the $V_L$ and $V_H$ domains of a single arm of an antibody; (4) a single chain Fv (scFv), which can be a single polypeptide chain composed of a $V_H$ domain and a $V_L$ domain through a peptide linker; and (5) a (scFv)$_2$, which can comprise two $V_H$ domains linked by a peptide linker and two $V_L$ domains, which are associated with the two $V_H$ domains via disulfide bridges.

The term "human antibody" refers to antibodies having variable and constant regions corresponding substantially to, or derived from, antibodies obtained from human subjects, e.g., encoded by human germline immunoglobulin sequences or variants thereof. The human antibodies described herein may include one or more amino acid residues not encoded by human germline immunoglobulin sequences (e.g., mutations introduced by random or site-specific mutagenesis in vitro or by somatic mutation in vivo). Such mutations may present in one or more of the CDRs, or in one or more of the FRs. In some examples the human antibodies may have at least one, two, three, four, five, or more positions replaced with an amino acid residue that is not encoded by the human germline immunoglobulin sequence.

An "isolated" substance means that it has been altered by the hand of man from the natural state. If an "isolated" substance presents in nature, it has been changed or removed from its original environment, or both. For example, a polypeptide naturally present in a living subject is not "isolated" but the polypeptide is isolated if it has been substantially separated from the coexisting materials of its natural state and exist in a substantially pure state.

The term "specific binds" or "specifically binding" refers to a non-random binding reaction between two molecules, such as the binding of the antibody to an epitope of the antigen. An antibody that "specifically binds" to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen or an epitope than it does with alternative targets/epitopes. An antibody "specifically binds" to a target antigen if it binds with greater affinity, avidity, more readily, and/or with greater duration than it binds to other substances. For example, an antibody that specifically (or preferentially) binds to an IgE epitope is an antibody that binds this IgE epitope with greater affinity, avidity, more readily, and/or with greater duration than it binds to other IgE epitopes or non-IgE epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

The terms "subject," "individual," and "patient" are used interchangeably herein and refer to a mammal being assessed for treatment and/or being treated. Subjects may be human, but also include other mammals, particularly those mammals useful as laboratory models for human disease, e.g. mouse, rat, rabbit, dog, etc.

The term "treatment" or "treating" refers to an action, application or therapy, wherein a subject, including a human being, is subjected to medical aid with the purpose of improving the subject's condition, directly or indirectly. Particularly, the term refers to reducing incidence, or alleviating symptoms, eliminating recurrence, preventing recurrence, preventing incidence, improving symptoms, improving prognosis or combination thereof in some embodiments. The skilled artisan would understand that treatment does not necessarily result in the complete absence or removal of symptoms. For example, with respect to cancer, "treatment" or "treating" may refer to slowing neoplastic or malignant cell growth, proliferation, or metastasis, preventing or delaying the development of neoplastic or malignant cell growth, proliferation, or metastasis, or some combination thereof.

An "effective amount" or an "effective dose" or a "therapeutically effective amount" in connection with administration of a pharmacological agent, as used herein, refers to an amount of a drug or pharmaceutical agent which, as compared to a corresponding subject who has not received such amount, results in an intended pharmacological result, or an effect in treatment, healing, prevention, or amelioration of a disease, disorder, or side effect, or a decrease in the rate of advancement of a disease or disorder. The effective amount or dose of a pharmacological agent may vary depending on particular active ingredient employed, the mode of administration, and the age, size, and condition of the subject to be treated. Precise amounts of a pharmacological agent are required to be administered depend on the judgment of the practitioner and are peculiar to each individual.

An "IL6 associated diseases or conditions" refer to any disease or condition in which IL6 plays a regulatory role in the signaling pathway leading to that disease or disorder. IL6 is a member of a family of cytokines that initiate cellular responses through a receptor complex composed of at least one subunit of the signal-transducing glycoprotein gp130 and the IL6 receptor (IL6R). IL6 binds to IL6R, which then dimerizes gp130 that triggers the phosphorylation of tyrosine residues of gp130. At least three major signaling pathways are involved in the formation of the IL6/IL6R/gp130 complex, (1) phosphatidyl inositol-3'-kinase (PI3K), (2) mitogen-activated protein kinase (MAK), and (3) Janus tyrosine kinase (JAK)-signal transducer and activator of transcription 1 and 3 (STAT1 and STAT3) pathway. IL6 is believed to play a role in the development of a wide range of disease or disorders, including but are not limited to, inflammation, autoimmune diseases (e.g. rheumatoid arthritis (RA), Crohn's disease, Castleman's disease, multiple sclerosis, ankylosing spondylitis, psoriatic arthritis and psoriasis), angiogenesis, cancer (e.g. multiple myeloma, leukemia, breast cancer, pancreatic cancer, lung cancer, ovarian cancer, oral cancer and prostate cancer), tumor metastasis, cancer related cachexia.

As used herein, "rheumatoid arthritis" refers to a type of autoimmune disease, which is characterized by synovial joint inflammations throughout the body. An early symptom of the disease is joint pain, which progresses into joint deformation, or damages in body organs such as in blood vessels, heart, lungs, skin, and muscles.

As used herein, "angiogenesis" generally refers to the fundamental process by which new blood vessels are formed. Angiogenesis can occur as a normal physiological process during periods of tissue growth, such as an increase in muscle, wound repair and pregnancy, but can also be associated to a disease condition where the growth of blood vessels is not beneficial to the health of the patient, such as cancer and diabetic retinopathy.

The term "cancer" as used herein refers to a medical condition mediated by neoplastic or malignant cell group, proliferation, or metastasis, including solid cancers and non-solid cancers. Examples of cancer include but are not limited to, lung cancer, kidney cancer, gastric cancer, breast cancer, brain cancer, prostate cancer, hepatocellular cancer, pancreatic cancer, cervical cancer, ovarian cancer, liver cancer, bladder cancer, cancer of the urinary tract, thyroid cancer, melanoma, head and neck cancer, colon cancer, leukemia, lymphomas and myelomas.

The term "cachexia" refers to a state of general ill health and malnutrition. It is usually associated with and induced by malignant cancer, and is characterized by severe loss of appetite, dramatic loss of body mass, especially lean body mass, and muscle wasting.

High Affinity Anti-IL6 Antibodies

Figure 3:
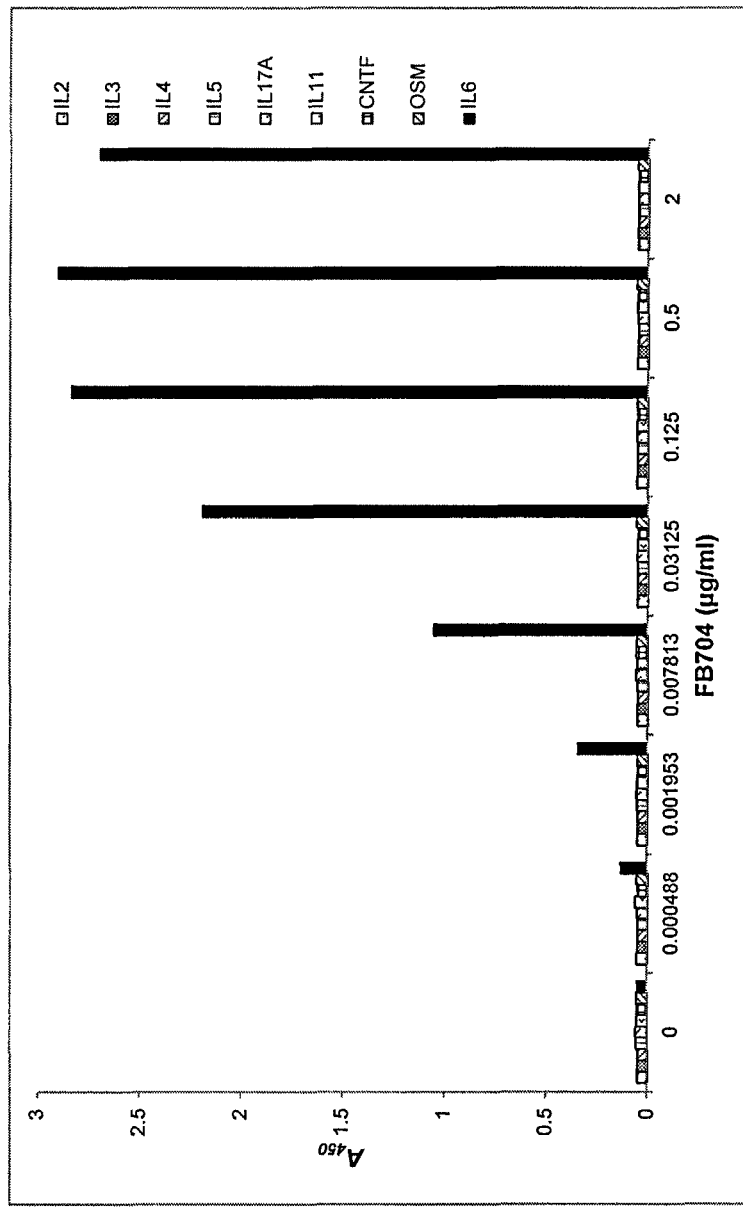
FIG. 3 is a diagram showing binding specificity of exemplary anti-IL6 antibodies described herein.
Figure 3:
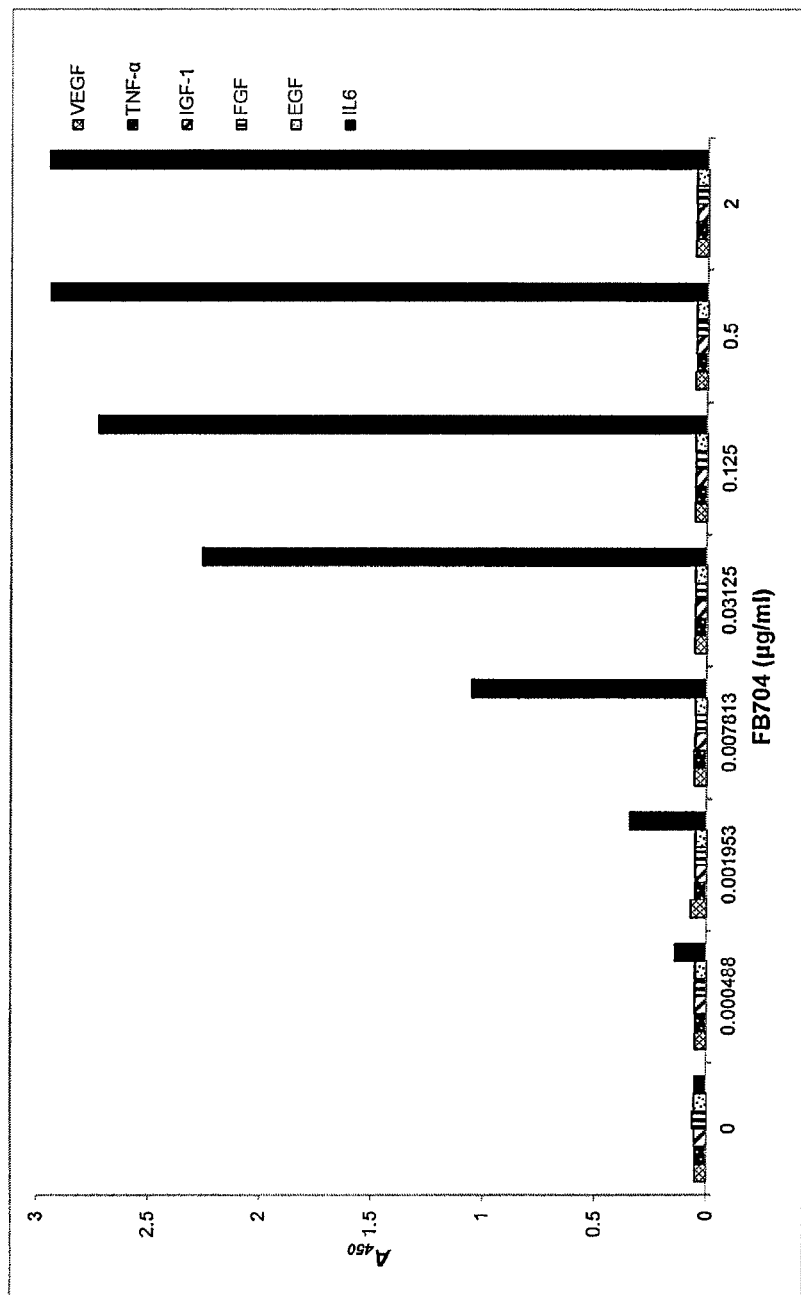

The present disclosure is based on the identification of a number of high affinity anti-IL6 antibodies, including 1-4-62, Ag1-4-6 (also known as FB704), and HAg1T-3-10. These anti-IL6 antibodies were found to bind to human IL-6 with high binding affinity (e.g., having a KD value less than $10^{-8}$ M, preferably less than $10^{-9}$ M) and high specificity, e.g., binding to other IL6 family cytokines such as those shown in FIG. 3 with a much lower binding affinity as compared with human IL6. Further, these antibodies were found to significantly reduce IL-6 induced cell proliferation and STAT3 phosphorylation, angiogenesis and hemoglobin production. Moreover, these anti-IL6 antibodies successfully suppressed cancer-induced (e.g., prostate cancer-induced) cachexia, pancreatic cancer growth, and cancer metastasis such as prostate cancer metastasis, significantly enhanced anti-cancer effects of other chemotherapeutic agents such as oxaliplatin, gemcitabine, and docetaxel, and reduced inflammatory cytokine (e.g., MCP-1 and sICAM) and/or VEGF production by HUVEC and PBMC cells and/or synovial fibroblasts, e.g., those obtained from RA patients.

Accordingly, described herein are high affinity antibodies capable of binding to (e.g., specifically binding to) human IL6, including 1-4-62, Ag1-4-6, and HAg1T-3-10, and their functional variants. The amino acid sequences of the heavy chain variable region ($V_H$) and light chain variable region ($V_L$) of each of 1-4-62, Ag1-4-6, and HAg1T-3-10 are shown in Table 1 below. A functional variant of any of these three antibodies can comprise a $V_H$ chain that comprises an amino acid sequence at least 85% (e.g., 90%, 92%, 94%, 95%, 96%, 97%, 98%, or 99%) identical to that of the $V_H$ of 1-4-62, Ag1-4-6, or HAg1T-3-10 (SEQ ID NO:17 or SEQ ID NO:18), a $V_L$ chain that has an amino acid sequence at least 85% (e.g., 90%, 92%, 94%, 95%, 96%, 97%, 98%, or 99%) identical to that of the $V_L$ of 1-4-62, Ag1-4-6, or HAg1T-3-10 (SEQ ID NO:19 or SEQ ID NO:20), or both. These variants are capable of binding to human IL6. In some examples, the variants possess similar antigen-binding affinity relative to the reference antibodies described above (e.g., having a $K_d$ less than $1 \times 10^{-8}$, preferably less than $1 \times 10^{-9}$ or $1 \times 10^{-10}$ M).

The affinity of the binding is defined by the terms ka (associate rate constant), kd (dissociation rate constant), or KD (equilibrium dissociation). Typically, specifically binding when used with respect to an antibody refers to an antibody that specifically binds to ("recognizes") its target(s) with an affinity (KD) value less than $10^{-8}$ M, e.g., less than $10^{-9}$ M or $10^{-10}$ M. A lower KD value represents a higher binding affinity (i.e., stronger binding) so that a KD value of $10^{-9}$ indicates a higher binding affinity than a KD value of $10^{-8}$.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

Antibodies binding to the same epitopes as 1-4-62, Ag1-4-6, and HAg1T-3-10 are also within the scope of the present disclosure.

In some embodiments, the anti-IL6 antibody comprises a heavy chain variable region ($V_H$) that comprises a HC CDR3 of MHIDDSNGYXSDAF (SEQ ID NO:21), in which X is an aromatic amino acid residue such as F, Y, H, or W. In some examples, the HC CDR3 is SEQ ID NO:6 or SEQ ID NO:16. The $V_H$ chain of such an antibody can further comprise a HC CDR1 of SEQ ID NO:2, a HC CDR2 of SEQ ID NO:2, or both.

Alternatively or in addition, the anti-IL6 antibody comprises a light chain variable region ($V_L$) that comprises a LC CDR3 of SEQ ID NO:13 or SEQ ID NO:15. The VL chain of such an antibody can further comprise a LC CDR1 of SEQ ID NO:9, a LC CDR2 of SEQ ID NO:11, or both.

In some embodiments, the anti-IL6 antibodies described herein comprises the same heavy chain and light CDRs as antibodies 1-4-62, Ag1-4-6, and HAg1T-3-10 as shown in Table 1 below. In some examples, these antibodies comprise the same $V_H$ and $V_L$ chains as 1-4-62, Ag1-4-6, and HAg1T-3-10. The $V_H$ and $V_L$ chains can be fused with heavy chain $C_H1$ and CL, respectively to form Fab, Fab' or F(ab')$_2$ fragments. Alternatively, the $V_H$ and $V_L$ chains can be fused with heavy chain constant region (e.g., human IgG constant chain) and light chain constant region (a kappa chain) to form full-length antibodies. In other examples, the $V_H$ and $V_L$ chains can be fused, either directly or via a linker, to form a single chain antibody.

In other embodiments, the functional variants described herein can contain one or more mutations (e.g., conservative substitutions) in the FRs of the $V_H$, the $V_L$, or both, as compared to those in antibodies 1-4-62, Ag1-4-6, and HAg1T-3-10. Preferably, such mutations do not occur at residues which are predicted to interact with one or more of the CDRs. As known in the art, mutations within the FR regions are unlikely to affect the antigen-binding activity of the antibody. In some examples, changes in one or more of the CDR regions of antibodies 1-4-62, Ag1-4-6, and HAg1T-3-10 are insubstantial, i.e., substantially identical to a reference sequence.

The term "insubstantial" or "substantially identical" means that the relevant amino acid sequences (e.g., in FRs, CDRs, $V_H$, or $V_L$ domain) of a variant differ insubstantially (e.g., including conservative amino acid substitutions) as compared with a reference antibody such that the variant has substantially similar binding activities (e.g., affinity, specificity, or both) and bioactivities relative to the reference antibody. Such a variant may include minor amino acid changes, e.g. 1 or 2 substitutions in a 5 amino acid sequence of a specified region.

Generally, more substitutions can be made in FR regions, in contrast to CDR regions, as long as they do not adversely impact the binding function of the antibody (such as reducing the binding affinity by more than 50% as compared to the original antibody). In some embodiment, the sequence identity can be about 85%, 90%, 95%, 96%, 97%, 98%, 99% or higher, between the original and the modified antibody. In some embodiments, the modified antibody has the same binding specificity and has at least 50% of the affinity of the original antibody. In some examples, the variant includes up to 5 amino acid substitutions such as conservative substitutions (e.g., 1, 2, 3, 4, or 5) in one or more CDR regions of the $V_H$, the $V_L$, or both of antibodies 1-4-62, Ag1-4-6, and HAg1T-3-10.

Conservative substitutions will produce molecules having functional and chemical characteristics similar to those of the molecule from which such modifications are made. For example, a "conservative amino acid substitution" may involve a substitution of a native amino acid residue with another residue such that there is little or no effect on the polarity or charge of the amino acid residue at that position. Desired amino acid substitutions (whether conservative or non-conservative) can be determined by those skilled in the art. For example, amino acid substitutions can be used to identify important residues of the molecule sequence, or to increase or decrease the affinity of the molecules described herein. Variants comprising one or more conservative amino acid substitutions can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The present disclosure also provides antibody variants with improved biological properties of the antibody, such as higher binding affinity. Amino acid sequence variants of the antibody can be prepared by introducing appropriate nucleotide changes into the antibody nucleic acid, or via peptide synthesis. Such modifications include, for example, deletions from, and/or insertions into and/or substitutions of, residues within the amino acid sequences of the antibody. Any combination of deletion, insertion, and substitution is made to achieve the final construct, provided that the final construct possesses the desired characteristics. Nucleic acid molecules encoding amino acid sequence variants of the antibody can be prepared by a variety of methods known in the art. These methods include, but are not limited to, oligonucleotide-mediated (or site-directed) mutagenesis, PCR mutagenesis, and cassette mutagenesis of an earlier prepared variant or a non-variant (natural) version of the antibody. In one embodiment, the equilibrium dissociation constant (KD) value of the anti-IL6 antibodies of the invention is less than $10^{-8}$ M, particularly less than $10^{-9}$ M or $10^{-10}$ M. The binding affinity may be determined using techniques known in the art, such as ELISA or biospecific interaction analysis, or other techniques known in the art.

Exemplary anti-IL6 antibodies as described herein include, but are not limited to:

(i) an antibody comprising (a) a $V_H$ comprising HC CDR1 that comprises the amino acid sequence set forth in SEQ ID NO: 2, HC CDR2 that comprises the amino acid sequence set forth in SEQ ID NO: 4, and HC CDR3 that comprises the amino acid sequence set forth in SEQ ID NO: 6 or SEQ ID NO: 16; or (b) a $V_L$ comprising a LC CDR1 that comprises the amino acid sequence set forth in SEQ ID NO: 9, a LC CDR2 that comprises the amino acid sequence set forth in SEQ ID NO: 11, and a LC CDR3 that comprises the amino acid sequence set forth in SEQ ID NO: 13 or SEQ ID NO: 15;

(ii) an antibody comprising a $V_H$ comprising a HC CDR1 that comprises the amino acid sequence set forth in SEQ ID NO: 2, a HC CDR2 that comprises the amino acid sequence set forth in SEQ ID NO: 4, and a HC CDR3 that comprises the amino acid sequence set forth in SEQ ID NO: 6;

(iii) an antibody comprising a $V_L$ comprising a LC CDR1 that comprises the amino acid sequence set forth in SEQ ID NO: 9, a LC CDR2 that comprises the amino acid sequence set forth in SEQ ID NO: 11, and a LC CDR3 that comprises the amino acid sequence set forth in SEQ ID NO: 13;

(iv) an antibody comprising (a) a $V_H$ comprising a HC CDR1 that comprises SEQ ID NO: 2, a HC CDR2 that comprises the amino acid sequence set forth in SEQ ID NO: 4, and a HC CDR3 that comprises the amino acid sequence set forth in SEQ ID NO: 6, and (b) a $V_L$ comprising a LC CDR1 that comprises the amino acid sequence set forth in SEQ ID NO: 9, a LC CDR2 that comprises the amino acid sequence set forth in SEQ ID NO: 11, and a LC CDR3 that comprises the amino acid sequence set forth in SEQ ID NO: 13;

(v) an antibody comprising a $V_L$ comprising a LC CDR1 that comprises the amino acid sequence set forth in SEQ ID NO: 9, a LC CDR2 that comprises the amino acid sequence set forth in SEQ ID NO: 11, and a LC CDR3 that comprises the amino acid sequence set forth in SEQ ID NO: 15;

(vi) an antibody comprising (a) a $V_H$ comprising a HC CDR1 that comprises the amino acid sequence set forth in SEQ ID NO: 2, a HC CDR2 that comprises the amino acid sequence set forth in SEQ ID NO: 4, and a HC CDR3 that comprises the amino acid sequence set forth in SEQ ID NO: 6, and (b) a $V_L$ comprising a LC CDR1 that comprises the amino acid sequence set forth in SEQ ID NO: 9, a LC CDR2 that comprises the amino acid sequence set forth in SEQ ID NO: 11, and a LC CDR3 comprising the amino acid sequence set forth in SEQ ID NO: 15;

(vii) an antibody comprising a $V_H$ comprising a HC CDR1 that comprises the amino acid sequence set forth in SEQ ID NO: 2, a HC CDR2 that comprises the amino acid sequence set forth in SEQ ID NO: 4, and a HC CDR3 that comprises the amino acid sequence set forth in SEQ ID NO: 16;

(viii) an antibody comprising a $V_H$ comprising (a) a HC CDR1 that comprises the amino acid sequence set forth in SEQ ID NO: 2, a HC CDR2 that comprises the amino acid sequence set forth in SEQ ID NO: 4, and a HC CDR3 that comprises the amino acid sequence set forth in SEQ ID NO: 16, and (b) a $V_L$ comprising a LC CDR1 that comprises the amino acid sequence set forth in SEQ ID NO: 9, a LC CDR2 that comprises the amino acid sequence set forth in SEQ ID NO: 11, and a LC CDR3 that comprises the amino acid sequence set forth in SEQ ID NO: 15.

Any of the anti-IL6 antibodies described herein can be examined to determine their properties, such as antigen-binding activity, antigen-binding specificity, and biological functions, following routine methods, e.g., those described in the examples below.

Any of the anti-IL6 antibodies described herein can be modified to contain additional nonproteinaceous moieties that are known in the art and readily available, e.g., by PEGylation, hyperglycosylation, and the like. Modifications that can enhance serum half-life are of interest.

Also disclosed herein are nucleic acids encoding any of the anti-IL6 antibodies described herein, vectors such as expression vectors comprising these nucleic acids, and host cells comprising the vectors. In one example, both the heavy and light chain coding sequences (e.g., sequences encoding a $V_H$ and a $V_L$, a $V_H$-$C_H$1 and a $V_L$-$C_L$, or a full-length heavy chain and a full-length light chain) are included in one expression vector. In another example, each of the heavy and light chains of the antibody is cloned into an individual vector. In the latter case, the expression vectors encoding the heavy and light chains can be co-transfected into one host cell for expression of both chains, which can be assembled to form intact antibodies either in vivo or in vitro. Alternatively, the expression vector encoding the heavy chain and that encoding the light chain can be introduced into different host cells for expression each of the heavy and light chains, which can then be purified and assembled to form intact antibodies in vitro.

Numerous methods known to those skilled in the art are available for obtaining antibodies or antigen-binding fragments thereof. For example, antibodies can be produced using recombinant DNA methods. Monoclonal antibodies may also be produced by generation of hybridomas. Hybridomas formed in this manner are then screened using standard methods, such as enzyme-linked immunosorbent assay (ELISA) to identify one or more hybridomas that produce an antibody that specifically binds with a specified antigen. In addition, phage display systems can be used to screen for single chain antibodies.

Alternatively, any of the anti-IL6 antibodies can be prepared via conventional methodology, e.g., recombination technology. For example, the polypeptide sequences provided herein (see, e.g., Table 1) for the exemplary antibodies described herein can be used to obtain suitable nucleic acid sequences encoding such, and the nucleic acids sequences can be cloned into suitable expression vectors via conventional recombinant technology for producing the antibodies in suitable host cells (e.g., bacterial cells, yeast cells, or mammalian cells such as CHO cells) by routine methods. The antibodies thus prepared can be isolated from the cells or the culture supernatants and their binding features and bioactivities can be examined also by routine technology.

In one example, phage display systems are used to select IL6 single chain antibodies. Once isolated, polynucleotides encoding specific IL6 scFvs may be cloned into expression vectors designed to express full length immunoglobulins and fragments thereof having the desired specificity. Briefly, the $V_H$ and $V_L$ polynucleotides of the single chain antibody are cloned into an immunoglobulin scaffold (i.e., IgG) vector, expressed, and dimerized so as to "convert" the single chain into a full antibody. The immunoglobulin scaffold may be selected from any of the five major classes of immunoglobulins (IgA, IgD, IgE, IgG and IgM) as needed. Methods for the conversion of scFvs into intact immunoglobulin molecules are well known, for example, as described in, WO 94/11523, WO 97/9351 or EP 0481790.

The recombinant vectors for expression the antibodies described herein typically contain a nucleic acid encoding the antibody amino acid sequences operably linked to a promoter, either constitutive or inducible. The vectors can be suitable for replication and integration in prokaryotes, eukaryotes, or both. Typical vectors contain transcription and translation terminators, initiation sequences, and promoters useful for regulation of the expression of the nucleic acid encoding the antibody. The vectors optionally contain generic expression cassettes containing at least one independent terminator sequence, sequences permitting replication of the cassette in both eukaryotes and prokaryotes, i.e., shuttle vectors, and selection markers for both prokaryotic and eukaryotic systems.

Recombinant anti-IL6 antibodies as described herein may be produced in prokaryotic or eukaryotic expression systems, such as bacteria, yeast, filamentous fungi, insect, and mammalian cells. It is not necessary that the recombinant antibodies of the invention be glycosylated or expressed in eukaryotic cells; however, expression in mammalian cells is generally preferred. Examples of useful mammalian host cell lines are human embryonic kidney line (293 cells), baby hamster kidney cells (BHK cells), Chinese hamster ovary cells/– or + DHFR (CHO, CHO-S, CHO-DG44, Flp-in CHO cells), African green monkey kidney cells (VERO cells), and human liver cells (Hep G2 cells). Host cells are transformed or transfected with the vectors (for example, by chemical transfection or electroporation methods) and cultured in conventional nutrient media (or modified as appropriate) for inducing promoters, selecting transformants, or amplifying the genes encoding the desired sequences. The antibody protein as produced can be further isolated or purified to obtain preparations that substantially homogeneous for further assays and applications. Standard protein purification methods known in the art can be used. For example, suitable purification procedures may include fractionation on immunoaffinity or ion-exchange columns, ethanol precipitation, high-performance liquid chromatography (HPLC), sodium dodecyl sulfate polyacrylamide gel electrophoresis (SDS-PAGE), ammonium sulfate precipitation, and gel filtration.

When a full-length antibody is desired, coding sequences of any of the anti-IL6 $V_H$ and $V_L$ chains described herein can be linked to the coding sequences of the Fc region of a human immunoglobulin and the resultant gene encoding a full-length antibody heavy and light chains can be expressed and assembled in a suitable host cell, e.g., a plant cell, a mammalian cell, a yeast cell, or an insect cell.

Antigen-binding fragments can be prepared via routine methods. For example, F(ab')$_2$ fragments can be produced by pepsin digestion of an full-length antibody molecule, and Fab fragments that can be generated by reducing the disulfide bridges of F(ab')$_2$ fragments. Alternatively, such fragments can be prepared via recombinant technology by expressing the heavy and light chain fragments in suitable host cells (e.g., *E. coli*, yeast, mammalian, plant, or insect cells) and have them assembled to form the desired antigen-binding fragments either in vivo or in vitro.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions.

Uses of Anti-IL6 Antibodies

Anti-IL6 antibodies as described herein were found to bind IL6 and act as antagonists to IL6 and regulate IL6 dependent signaling pathway. In particularly, those antibodies were found to significantly inhibit IL6-dependent cell proliferation (e.g., pancreatic cancer cell growth) and phosphorylated STAT signaling transduction, decrease IL6-induced angiogenic formation in vivo, and suppress human tumor metastasis (e.g., prostate cancer metastasis). Further, these antibodies exhibited synergistic efficacy when co-used with a chemotherapeutic agent, such as oxaliplatin, gemcitabine, and docetaxel, in animal models of human pancreatic tumor.

Therefore, the anti-IL6 antibodies described herein can be used in treating a disease or condition associated with IL6, including, but are not limited to, inflammatory disorder, autoimmune diseases (e.g. rheumatoid arthritis (RA), Crohn's disease, Castleman's disease, multiple sclerosis, ankylosing spondylitis, psoriatic arthritis and psoriasis), angiogenesis, cancer such as a solid tumor (e.g. multiple myeloma, leukemia, breast cancer, pancreatic cancer, lung cancer, ovarian cancer, oral cancer and prostate cancer), tumor metastasis, and cancer related cachexia.

To practice the treatment methods described herein, any of the anti-IL6 antibodies (e.g., an antibody having the same CDRs or same $V_H$ and $V_L$ chains as antibodies 1-4-62, Ag1-4-6, or HAg1T-3-10), or a nucleic acid(s) (e.g., an expression vector) encoding such an antibody can be formulated into a pharmaceutical composition with one or more pharmaceutically acceptable carriers. "Pharmaceutically acceptable" as used herein means that the carrier is compatible with the active ingredient contained in the composition, preferably capable of stabilizing the active ingredient, and not deleterious to the subject to be treated. The carrier may serve as a diluent, vehicle, excipient, or medium for the active ingredient. Some examples of suitable carriers include physiologically compatible buffers, such as Hank's solution, Ringer's solution, physiological saline buffer, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The pharmaceutical composition can additionally include lubricating agents such as talc, magnesium stearate, and mineral oil; wetting agents; emulsifying and suspending agents; preserving agents such as methyl- and propylhydroxy-benzoates; sweetening agents; and flavoring agents. See, e.g., Remington's Pharmaceutical Sciences, Edition 16, Mack Publishing Co., Easton, Pa. (1980); and Goodman and Gilman's "The Pharmacological Basis of Therapeutics", Tenth Edition, Gilman, J. Hardman and L. Limbird, eds., McGraw-Hill Press, 155-173, 2001.

The pharmaceutical composition according to the invention can be in the form of tablets, pills, powders, lozenges, sachets, cachets, elixirs, suspensions, emulsions, solutions, syrups, soft and hard gelatin capsules, suppositories, sterile injectable solutions, and packaged powders. The pharmaceutical composition of the invention may be delivered through any physiologically acceptable route. These routes can include, but are by no means limited to parenteral administration, systemic administration, oral administration, nasal administration, rectal administration, intraperitoneal injection, intravascular injection, subcutaneous injection, transcutaneous administration, inhalation administration, and intramuscular injection. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The pharmaceutical compositions, formulated for therapeutic uses, may be prepared for storage by mixing an agent having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some embodiments, the method described herein aims at treating cancer, such as prostate cancer. A human subject who needs this treatment can be a patient suffering from or is suspected of having cancer. In some examples, the amount of the anti-IL6 antibody described herein is effective in inhibiting IL6-induced cell proliferation by at least 20%, 30%, 50%, 80%, 100%, 200%, 400%, or 500% as compared to a blank control. In other embodiments, the amount of the anti-IL6 antibody described herein is effective in inhibiting STAT3 phosphorylation by at least 20%, 30%, 50%, 80%, 100%, 200%, 400%, or 500%. In some examples, the amount of the anti-IL6 antibody described herein is effective in inhibiting IL6-induced angiogenesis, cancer-induced cachexia (e.g., prostate cancer-induced cachexia), cancer metastasis (prostate cancer metastasis), or a combination thereof.

In other embodiment, the method described herein is for treating an autoimmune disease, such as rheumatoid arthritis. In another example, the subject is a human rheumatoid arthritis patient who suppers from or is suspected of having the disease. In some example, the amount of the anti-IL6 antibody described herein is sufficient in reducing the production of inflammatory cytokines such as MCP-1 and/or sICAM, e.g., by at least 20%, 30%, 50%, 80%, 100%, 200%, 400%, or 500%.

To treating a target disease such as cancer or rheumatoid arthritis, an effective amount of the pharmaceutical composition noted above can be administered to a subject (e.g., a human) in need of the treatment via a suitable route. A human subject who needs the treatment may be a human patient having, at risk for, or suspected of having a disorder associated with IL6. Such a patient can be identified by routine medical examination.

Any of the anti-IL6 antibodies as described herein may be used in combination with another therapeutic agent. The term "in combination" in this context means that the antibody composition and the therapeutic agent are given either simultaneously or sequentially. For example, the combination therapy can include at least one anti-IL6 antibody co-formulated with and/or co-administered with, at least one additional therapeutic agent. In one embodiment, the additional agent is a cancer chemotherapeutic agent e.g. oxaliplatin, gemcitabine, docetaxel. In another embodiment, the additional agent can be disease modifying antirheumatic drugs (DMARDs) e.g. methotrexate, azathioprine, chloroquine, hydroxychloroquine, cyclosporin A, sulfasalazine, for RA treatment. Such combination therapies may advantageously utilize lower dosages of the administered therapeutic agents, thus preventing possible toxicities or complications associated with the various monotherapies. Moreover, the additional therapeutic agents disclosed herein may act on pathways in addition to or distinct from the IL6/I6R/gp130 pathway, and thus are expected to enhance and/or synergize with the effects of the anti-IL6 antibodies.

When the antibody composition described here is co-used with a second therapeutic agent, a sub-therapeutic dosage of either the composition or of the second agent, or a sub-therapeutic dosage of both, can be used in the treatment of a subject having, or at risk of developing a disease or disorder associated with the cell signaling mediated by IL6. A "sub-therapeutic dose" as used herein refers to a dosage, which is less than that dosage which would produce a therapeutic result in the subject if administered in the absence of the other agent or agents. Thus, the sub-therapeutic dose of an agent is one which would not produce the desired therapeutic result in the subject in the absence of the administration of the anti-IL6 antibody described herein. Therapeutic doses of many agents that are in clinical use are well known in the field of medicine, and additional therapeutic doses can be determined by those of skill without undue experimentation. Therapeutic dosages have been extensively described in references such as Remington's Pharmaceutical Sciences, 18th ed., 1990; as well as many other medical references relied upon by the medical profession as guidance for the treatment of diseases and disorders.

Conventional methods, known to those of ordinary skill in the art of medicine, can be used to administer the pharmaceutical composition to the subject, depending upon the type of diseases to be treated or the site of the disease.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

When a nucleic acid(s) encoding an anti-IL6 antibody as described herein is used as the therapeutic agent, the nucleic acid(s) or a vector(s) expressing the antibody can be delivered to a subject by methods, such as that described in Akhtar et al., 1992, Trends Cell Bio. 2, 139. For example, it can be introduced into cells using liposomes, hydrogels, cyclodextrins, biodegradable nanocapsules, or bioadhesive microspheres. Alternatively, the nucleic acid or vector can be locally delivered by direct injection or by use of an infusion pump. Other approaches include employing various transport and carrier systems, for example through the use of conjugates and biodegradable polymers.

To facilitate delivery, any of the anti-IL6 antibody or its encoding nucleic acids can be conjugated with a chaperon agent. As used herein, "conjugated" means two entities are associated, preferably with sufficient affinity that the therapeutic benefit of the association between the two entities is realized. Conjugated includes covalent or noncovalent bonding as well as other forms of association, such as entrapment of one entity on or within the other, or of either or both entities on or within a third entity (e.g., a micelle).

The chaperon agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, and polyphosphazine.

In one example, the chaperon agent is a micelle, liposome, nanoparticle, or microsphere, in which the oligonucleotide/interfering RNA is encapsulated. Methods for preparing such a micelle, liposome, nanoparticle, or microsphere are well known in the art. See, e.g., U.S. Pat. Nos. 5,108,921; 5,354, 844; 5,416,016; and 5,527,5285.

In another example, the chaperon agent serves as a substrate for attachment of one or more of a fusogenic or condensing agent.

A fusogenic agent is responsive to the local pH. For instance, upon encountering the pH within an endosome, it can cause a physical change in its immediate environment, e.g., a change in osmotic properties which disrupts or increases the permeability of the endosome membrane, thereby facilitating release of the antisense oligonucleotide into host cell's cytoplasm. A preferred fusogenic agent changes charge, e.g., becomes protonated at a pH lower than a physiological range (e.g., at pH 4.5-6.5). Fusogenic agents can be molecules containing an amino group capable of undergoing a change of charge (e.g., protonation) when exposed to a specific pH range. Such fusogenic agents include polymers having polyamino chains (e.g., polyethyleneimine) and membrane disruptive agents (e.g., mellittin). Other examples include polyhistidine, polyimidazole, polypyridine, polypropyleneimine, and a polyacetal substance (e.g., a cationic polyacetal).

A condensing agent interacts with the antisense oligonucleotide, causing it to condense (e.g., reduce the size of the oligonucleotide), thus protecting it against degradation. Preferably, the condensing agent includes a moiety (e.g., a charged moiety) that interacts with the oligonucleotide via, e.g., ionic interactions. Examples of condensing agents include polylysine, spermine, spermidine, polyamine or quarternary salt thereof, pseudopeptide-polyamine, peptidomimetic polyamine, dendrimer polyamine, arginine, amidine, protamine, cationic lipid, cationic porphyrin, and alpha helical peptide.

The anti-IL6 antibodies described herein may also be used to detect the presence of IL6 in biological samples. Antibody-based detection methods are well known in the art, and include, for example, ELISA, immunoblots, radioimmunoassays, immunofluorescence, immunoprecipitation, and other related techniques. The antibodies may be provided in a diagnostic kit that incorporates at least one other components to detect the protein. The kit may also contain packaging, instructions, or other material to aid the detection of the protein and use of the kit.

Antibodies may be modified with detectable markers, including ligand groups (e.g., biotin), radioisotopes, fluorophores, or enzymes. Enzymes are detected by their activity. For example, horseradish peroxidase is detected by its ability to convert the substrate, tetramethylbenzidine (TMB), to a blue pigment, which is quantifiable with a spectrophotometer. Antibodies can also be functionally linked (e.g., by genetic fusion, chemical coupling, non-covalent association or otherwise) to at least one other molecule(s), such as another antibody (e.g., a bispecific or a multispecific antibody), cytotoxic or cytostatic agents, toxins, radioisotopes and the like.

Kits

The present disclosure also provides kits for use in treating diseases associated with IL6. Such kits can include one or more containers comprising an anti-IL6 antibody (e.g., 1-4-62, Ag1-4-6, and HAg1T-3-10) or its encoding nucleic acid.

In some embodiments, the kit can comprise instructions for use in accordance with any of the methods described herein.

The included instructions can comprise a description of administration of the anti-IL6 antibody to treat, delay the onset, or alleviate a disease associated with IL6 such as cancer (e.g., prostate cancer) or an autoimmune disease (e.g., RA) according to any of the methods described herein. The kit may further comprise a description of selecting an individual suitable for treatment based on identifying whether that individual has the disease. In still other embodiments, the instructions comprise a description of administering an anti-IL6 antibody an individual at risk of the disease.

The instructions relating to the use of an anti-IL6 antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating liver fibrosis or cirrhosis. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-IL6 antibody.

Any of the kit described herein may further include an additional therapeutic agent, such as an anti-cancer drug (e.g., oxaliplatin, gemcitabine, or docetaxel) or a DMARD (e.g., methotrexate, azathioprine, chloroquine, hydroxychloroquine, cyclosporine A, or sulfasalazine).

Kits may optionally provide additional components such as buffers and interpretive information. Normally, the kit comprises a container and a label or package insert(s) on or associated with the container. In some embodiments, the invention provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1

Identification of High Affinity Antibodies Binding to Human IL6

A phage-displayed human naïve scFv library was constructed as follows for identifying high affinity human antibodies capable of binding to human IL6.

mRNAs were isolated from peripheral blood lymphocytes of 151 health donors and cDNAs were synthesized from such by M-MuLV reverse transcriptase (Fermentas) using oligo dT primers. $V_H$ and $V_L$ genes were amplified, assembled, and ligated into a phagemid vector by standard protocols with some modifications. The ligated products were introduced into TG1 E-coli cells via electroporation. Afterwards, the E. coli cells were recovered and incubated in the 2YT medium containing 100 mg/ml ampicillin and 2% glucose. M13KO7 helper phage particles were added to the culture to generate scFv-phage particles, thus producing an scFv library. The diversity of the library was determined by sequencing over 1,000 clones.

The scFv library was subjected to four rounds of biopanning as follows. Wells were coated with recombinant IL6 in 0.1M NaHCO3 buffer at 4° C. overnight and then rinsed twice with 300 μl of phosphate buffered saline (PBS). The wells were blocked with 1% bovine serum albumin (BSA) in PBS for 1 h at 37° C.; added with 100 μl of the phage particles ($2\times10^{11}$ pfu) in PBS containing 1% BSA, and rocked for 1 h at room temperature (RT). The wells were then washed 6 times with 300 μl 0.5% (w/v) Tween 20/PBS. Bound phages were eluted and amplified by infection with E. coli TG1. The infected cells were rescued by M13KO7. The resultant phage particles were concentrated via PEG-precipitation and used for the next round of biopanning.

In the fourth and fifth rounds of biopanning, the phage clones were examined by Enzyme-linked immunosorbent assay (ELISA) screening for their antigen-binding specificities. ELISA plates were coated with recombinant human IL6 or BSA at 2 μg/ml in 0.1M NaHCO3 buffer at 4° C. overnight. After being washed by PBS, the wells were blocked with 1% (w/v) BSA in PBS for 1 h at RT. Phage clones and scFv fragments were added to the plates, which were incubated for 1 h at RT. The plate was washed by PBS containing 0.1% (v/v) Tween 20 and then probed with HRP-labeled goat anti-human IgG (KPL) diluted 1:10,000 in 1% BSA-PBS for 40 min at RT. The plate was again washed and 3,3',5,5'-Tetramethylbenzidine (TMB) substrate solution was added to develop color. Stop solution (1M $H_2SO_4$) was then added and the absorption at 450 nm was quantitated using an automated plate photometer (Bio-Rad).

After four rounds of biopanning, more than eight hundred phage clones were identified as capable of binding to the rhIL6 by the ELISA assay described above. 29 phage clones were selected for sequence analysis to determine the $V_H$ and $V_L$ sequences encoding anti-IL6 antibodies. A number of unique clones were identified; their binding activity and specificity were determined by a comparative ELISA assay.

A parent phage clone identified from the biopanning procedures described above, clone 1-4-62, was selected for affinity maturation to produce high affinity anti-IL6 antibodies via construction via site-directed mutagenesis of randomized $V_L/V_H$ CDR phage antibody libraries, each containing more than $0.9\times10^9$ variant antibodies. The libraries were constructed using $V_L$ and $V_H$ forward primers containing randomized sequences at the CDR regions based on the $V_L$ and $V_H$ sequences of clone 1-4-62, following standard protocols below. The CDR randomized libraries were subjected to the biopanning procedures under high stringency conditions as described herein and at least two high affinity clones, Ag1-4-6 (FB704) and Hag1T-3-10 were identified as having higher binding activities relative to the parent clone.

The complementary determining regions 1-3 (CDR 1-3) and framework regions 1-4 (FW1-4) for both the $V_H$ and $V_L$ domains for the three anti-IL6 antibodies, 1-4-62, Ag1-4-6, and Hag1T-3-10, are provided in Table 1 below:

TABLE 1

Amino acid sequences of $V_H$ and $V_L$ domains for anti-IL6 antibodies $V_H$ domain

| | FW1 | CDR1 | FW2 | CDR2 |
|---|---|---|---|---|
| 1-4-62 | EVQLVESGPALVKPTQT LTLTCTFSGFSLS (SEQ ID NO: 1) | TGGMSVS (SEQ ID NO: 2) | WIRQPPGKALEWLA (SEQ ID NO: 3) | RIDWDDDKFYTPS LKT (SEQ ID NO: 4) |
| Ag1-4-6 | EVQLVESGPALVKPTQT LTLTCTFSGFSLS (SEQ ID NO: 1) | TGGMSVS (SEQ ID NO: 2) | WIRQPPGKALEWLA SEQ ID NO: 3) | RIDWDDDKFYTPS LKT (SEQ ID NO: 4) |
| HAg1T-3-10 | EVQLVESGPALVKPTQT LTLTCTFSGFSLS (SEQ ID NO: 1) | TGGMSVS (SEQ ID NO: 2) | WIRQPPGKALEWLA (SEQ ID NO: 3) | RIDWDDDKFYTPS LKT (SEQ ID NO: 4) |

| | FW3 | CDR3 | FW4 |
|---|---|---|---|
| 1-4-62 | RLTISRDTSKNQVVLIMT NMDPVDTATYYCAR (SEQ ID NO: 5) | MHIDDSNGYYSDAFHI (SEQ ID NO: 6) | WGQGTMVTVSS (SEQ ID NO: 7) |
| Ag1-4-6 | RLTISRDTSKNQVVLIMT NMDPVDTATYYCAR (SEQ ID NO: 5) | MHIDDSNGYYSDAFHI (SEQ ID NO: 6) | WGQGTMVTVSS (SEQ ID NO: 7) |
| HAg1T-3-10 | RLTISRDTSKNQVVLIMT NMDPVDTATYYCAR (SEQ ID NO: 5) | MHIDDSNGYFSDAFHI (SEQ ID NO: 16) | WGQGTMVTVSS (SEQ ID NO: 7) |

$V_L$ domain

| | FW1 | CDR1 | FW2 | CDR2 |
|---|---|---|---|---|
| 1-4-62 | EIVLTQSPATLSVSPGER VTLSC (SEQ ID NO: 8) | RDSQSVSSTSLA (SEQ ID NO: 9) | WYQQKSGQAPRLLIY (SEQ ID NO: 10) | DTSNRAT (SEQ ID NO: 11) |
| Ag1-4-6 | EIVLTQSPATLSVSPGER VTLSC (SEQ ID NO: 8) | RDSQSVSSTSLA (SEQ ID NO: 9) | WYQQKSGQAPRLLIY (SEQ ID NO: 10) | DTSNRAT (SEQ ID NO: 11) |
| HAg1T-3-10 | EIVLTQSPATLSVSPGER VTLSC (SEQ ID NO: 8) | RDSQSVSSTSLA (SEQ ID NO: 9) | WYQQKSGQAPRLLIY (SEQ ID NO: 10) | DTSNRAT (SEQ ID NO: 11) |

| | FW3 | CDR3 | FW4 |
|---|---|---|---|
| 1-4-62 | GIPARFSGGGSGTDFTL TISSLEPEDFAVYYC (SEQ ID NO: 12) | LVRNNWPPRFT (SEQ ID NO: 13) | FGQGTKVEIK (SEQ ID NO: 14) |
| Ag1-4-6 | GIPARFSGGGSGTDFTL TISSLEPEDFAVYYC (SEQ ID NO: 12) | SFVSRPYPRFT (SEQ ID NO: 15) | FGQGTKVEIK (SEQ ID NO: 14) |
| HAg1T-3-10 | GIPARFSGGGSGTDFTL TISSLEPEDFAVYYC (SEQ ID NO: 12) | SFVSRPYPRFT (SEQ ID NO: 15) | FGQGTKVEIK (SEQ ID NO: 14) |

Example 2

Characterization of High Affinity Antibodies Binding to Human IL6

Materials and Methods (i) Cell Lines and Antibodies

The human myeloma cells, U266 cell line (BCRC 60437), were obtained from the Bioresource Collection and Research Center (BCRC) in Taiwan and were cultured in RPMI 1640 (Biowet) supplemented with 10% fetal bovine serum.

The IL6-dependent B cell hybridoma, B9, was cultured in RPMI 1640 supplemented with 5% fetal bovine serum plus 50 pg/ml recombinant human IL6.

Human umbilical vein endothelial cells (HUVECs) were purchased from Lonza and were grown on gelatin-coated petridish in EGM™-2 singleQuots® medium (Lonza).

The IgG producing cells, FreeStyle™ CHO cell line (Invitrogen), were cultured in FreeStyle™ CHO expression medium (Invitrogen) with 8 mM L-glutamine.

Flp-in CHO cell line (Invitrogen) were cultured in Ham's F12 (Invitrogen) with 10% fetal bovine serum.

A control anti-IL6 antibody, BE8, was purchased from Diaclone. Actemra, an antibody drug (anti-IL6 antibodies) approved by the U.S. Food and Drug Administration (FDA) for treating rheumatoid arthritis, was purchased from Universitatsklinikum Heidelberg, Germany. Human IgG1 nucleotide was purchased from Sigma.

(ii) Production of Fully Human Anti-IL6 IgG1 Antibodies

Four expressed vectors (pA01-Kappa, pA02-Gamma, p2CMV intermediate and modified pcDNAFRT) were constructed for producing human IgG in mammalian cells. The whole light chain gene (containing a Kappa constant region)

and the whole heavy chain gene (containing a gamma constant region) encoding anti-IL6 candidate antibodies were cloned from pcANTABSE into pA01-Kappa and pA02-Gamma separately for transient antibody expression. These expression vectors were introduced into FreeStream™ CHO-S cells by GenJet™ Plus reagent (SignalGen).

The whole light chain and heavy chain genes were first cloned into p2CMV intermediate vector and then cloned into a modified pcDNAFRT single expression vector for stable antibody expression. The pcDNAFRT vector was transfected into CHO cells by GenJet™ Plus reagent and positive clones were selected with Hygromycin B (Invitrogen) for a longer period of time expression. The culture supernatant was harvested and purified by MabSelect SuRe and protein A columns (GE Healthcare).

(iii) Binding and Competition Analysis

ELISA and Western blot were performed to examine the binding activity of anti-IL6 human IgG antibodies. Briefly, plates were coated with recombinant human IL6 (R&D Systems) at 2 µg/ml. After being washed by PBS, the wells were blocked with 1% (w/v) BSA in PBS for 1 h at RT. Purified anti-IL6 antibodies in serial dilutions (starting concentration of 2 µg/ml) were placed into the wells and incubated at RT for 1 h. The plate was washed by PBS containing 0.1% (w/v) Tween 20 and then probed with HRP-labeled goat anti-human IgG (KPL), which was diluted 1:10,000 in 1% BSA-PBS, for 40 min at RT. The plate was again washed and a TMB substrate solution was added to develop color. Stop solution (1M $H_2SO_4$) was then added and the absorption at 450 nm was quantitated using an automated plate photometer (Bio-Rad).

Recombinant IL6 protein was boiled in 5× reducing sample buffer (0.15 M Tris-HCl, pH 6.8, 50% glycerol, 10% SDS, 0.71 M 2-mercaptoethanol, 0.095% bromophenol blue) for 10 min, and subjected to SDS-PAGE (Bio-Rad). The proteins were then transferred to a nitrocellulose membrane (Bio-Rad), and immunoblotted with the fully-human anti-IL6 antibodies described herein. After being incubated with HRP-labeled goat anti-rabbit (Thermo) or HRP-labeled goat anti-mouse (KPL) antibody, the membranes were developed by enhanced chemiluminescence (GE Healthcare).

Plates were coated with recombinant human IL6 receptor-α (R&D Systems) at 2 µg/ml in 0.1M NaHCO3 buffer at 4° C. overnight. After being washed by PBS, the wells were blocked with 1% (w/v) BSA in PBS for 1 h at RT. Purified anti-IL6 antibodies in two-fold serial dilutions at a starting concentration of 2 µg/ml were pre-incubated with rhIL6 (0.5 µg/ml) at RT for 1 hr. The mixtures were the placed into the plate and incubated at RT for 1 h. The plate was washed by PBS containing 0.1% (v/v) Tween 20 and then probed with mouse anti-human IL-6 IgG2a (Abcam) diluted 1:2,000 in 1% BSA-PBS for 1 h at RT. The plate was washed and then probed with HRP-labeled goat anti-mouse IgG (Thermo) diluted 1:10,000 in 1% BSA-PBS for 40 min at RT. The plate was again washed and a TMB substrate solution was added to develop color. Stop solution (1M $H_2SO_4$) was then added and the absorption at 450 nm quantitated using an automated plate photometer.

(iv) Cell Signaling Transduction Assay

U266 cells (1×106/ml) were washed twice with serum-free RPMI 1640 and cultured for 2 h in the absence of fetal bovine serum and growth factors. Cells were stimulated with rhIL6 (5 ng/ml) for 30 min at 37° C. and then treated with or without anti-IL6 antibodies. Cells were washed with ice-cold PBS, and then lysed in RIPA buffer (Thermo) supplemented with protease and phosphatase inhibitor (Roche). Western blot analysis was performed using anti-pSTAT3, and anti-STAT3 (Cell Signaling Technology) antibodies. After incubating with HRP-labeled goat anti-rabbit (Thermo) or HRP-labeled goat anti-mouse antibody (Thermo), the membranes were developed by enhanced chemiluminescence (GE Healthcare).

(v) Cell Proliferation Assay

Murine B9 cells (5×104/ml) were seed in 96-well plates and incubated with rhIL6 (10 pg/ml). The IL6 receptor of murine B9 cell could be stimulated by human IL6. Anti-IL6 antibodies at various concentrations or control IgG antibodies were placed into to the wells. The cells were then cultured at 37° C. for 72 h. The cell viability was detected by Water Soluble Tetrazolium (WST-1) assay (Roche) according to manufacturer's instruction. All experiments were carried out in triplicates.

(vi) Biacore Analysis

IgG binding affinity was measured by using human antibody capture kit (GE healthcare) in BIAcore T200 system (GE healthcare). The mouse anti-human IgG was immobilized on a CM5 sensor chip via amine coupling. Approximately 700 RU of purified anti-IL6 IgG in HBS-EP+ buffer were captured onto the immobilized surface. The recombinant human IL6 (R&D Systems) at concentrations ranging from 25.6 nM to 0.4 nM in HBS-EP+ buffer was injected for 2 minutes using a flow rate of 30 µl/min. Dissociation of bound antigen in HBS⁻EP⁺ buffer flow was followed for 7 minutes. The surfaces IgG were regenerated after each cycle using regeneration solution (3M $MgCl_2$). The dissociation constant (KD) was calculated as kd/ka.

(vii) Specificity Analysis

Plates were coated with recombinant human IL3, IL4, IL5, IL6, IL11, IL17A, CNTF, OSM, IGF-1 (R&D Systems), IL2, FGF (Prospec), VEGF, TNF-α, EGF (Peprotech) at 2 µg/ml in 0.1M NaHCO3 buffer at 4° C. overnight. After being washed by PBS, the wells were blocked with 1% (w/v) BSA in PBS at RT for 1 h. Purified anti-IL6 antibodies in four-fold serial dilutions at a starting concentration of 2 µg/ml were placed into the wells and incubated at RT for 1 h. The plate was washed in PBS containing 0.1% (w/v) Tween 20 and then probed with HRP-labeled goat anti-human IgG (KPL) diluted 1:10,000 in 1% BSA-PBS for 40 min at RT. The plate was again washed and a TMB substrate solution was added to develop color. Stop solution (1M $H_2SO_4$) was then added and the absorption at 450 nm quantitated using VERSA max (Molecular Devices).

Results (a) Binding Activity of Anti-IL6 IgG Antibodies

To explore the binding specificity of anti-IL6 antibodies, $V_H$ and $V_L$ genes encoding the selected scFv clones were fused with kappa and gamma constant region genes to produce whole human IgG1 antibodies as described herein. ELISA and western blot assays showed that those anti-IL6 antibodies could bind human recombinant IL6 protein and exhibited neutralization activity in a dose-dependent manner.

The BIAcore analysis showed the average of association rate constants (ka) of clones Ag1-4-6 and Hag1T-3-10 were enhanced from $4.38 \times 10^{-5}$ to $2.24 \times 10^{-6}$ $M^{-1}$ $s^{-1}$ as compared with the parent 1-4-62 clone. The dissociation rate constants (kd) were enhanced from $1.66 \times 10^{-3}$ to $6 \times 10^{-4}$ $s^{-1}$. The equilibrium dissociation constants (KD) were improved from 3.85 to 0.27 nM. See Table 2 below.

TABLE 2

Associate rate constants (ka) and dissociation constants (kd) of anti-IL6 antibodies

| Antibody | Ka (1/Ms) | Kd (1/s) | KD (nM) |
|---|---|---|---|
| 1-4-62 | 4.38E+05 | 1.66E−03 | 3.85 |
| Ag1-4-6 | 1.61E+06 | 1.21E−03 | 0.75 |
| HAg1T-3-10 | 2.24E+06 | 6.00E−04 | 0.27 |

(b) Binding Specificity of Anti-IL6 Antibodies

An ELISA assay as described herein was performed to confirm the binding specificity of high-affinity anti-IL6 antibodies described herein. Briefly, plates were coated with different cytokines as indicated in FIG. 3A (IL6 family cytokines) and FIG. 3B (non-IL6 family cytokines) and the binding activities of the FB704 antibody clone (i.e. Ag1-4-6) to those cytokines were examined. FB704 showed high binding activity to human IL6 protein but not to other cytokines (FIGS. 3A and 3B), indicating its binding specificity to human IL6.

(c) Inhibition of IL6-Dependent Signaling Pathway and Cell Proliferation by Anti-IL6 Antibodies Human multiple myeloma U266 cells were used to examine the effect of anti-IL6 antibodies on IL6-induced signaling cascade. U266 cells were cultured in the presence or absent of antibodies, together with rhIL6. After 30 minutes, whole cell lysates were collected and western blot analysis was performed to examine phosphorylated STAT3 protein (P-STAT3), which is a major transcription factor involved in the IL6 signaling pathway. P-STAT3 protein expression was suppressed by the high affinity anti-IL6 antibodies, Ag1-4-6 and HAg1T-3-10, at a level greater than Actemra, an anti-IL6 receptor humanized antibody, was used as a control. (FIGS. 1A and 1B). The levels of inhibiting STAT3 phosphorylation by the antibodies are shown in Table 3 below:

TABLE 3

Levels of STAT3 phosphorylation inhibition by anti-IL6 antibodies

| inhibition percentage of control in different Ab concentration | 0.05 µg/ml | 0.5 µg/ml |
|---|---|---|
| 1-4-62 | 0 | 8 |
| Ag1-4-6 | 0 | 60 |
| HAg1T-3-10 | 49 | 93 |
| Actemra | 0 | 17 |

In addition, to examine the antibody activity on cell proliferation, IL6-dependent B9 murine hybridoma cells were cultured in the presence of anti-IL6 or anti-IL6R antibodies, as well as an isotype control antibody at various concentrations. The impact on cell proliferation was assessed by WST-1 assay (Roche) after 72 hours. As shown in FIG. 1C, fully-human anti-IL6 antibodies 1-4-62, Ag1-4-6, and HAg1T-3-10 inhibited B9 cell proliferation in a dose-dependent manner and the $IC_{50}$ values of 1-4-62, Ag1-4-6, and HAg1T-3-10 are 0.618, 0.0468, and 0.00456 µg/ml, respectively.

Example 3

Effectiveness of High Affinity Anti-IL6 Antibodies in Cancer Treatment

Materials and Methods (i) Animals

Male NOD/SCID mice (7-8 weeks old) were purchased from BioLASCO Taiwan Co., Ltd (Taipei, Taiwan) for all experiments. The mice were maintained in sterile individually ventilated cages (IVC) at 20° C. and acclimated to the housing facilities at least 7 days before experiments were initiated.

(ii) Matrigel Angiogenesis Assay

Liquid matrigel (BD Biosciences) was maintained at 4° C. hIL6 recombinant protein (R&D Systems) was added to Matrigel to a final concentration of 100 ng/0.5 ml. Mice were anesthetized with Avertin (0.2 ml/10 g, i.p. injection) and injected at two sites of the dorsal side with 0.5 ml of matrigel. Then, the mice were treated with anti-IL6 IgG antibodies or a control IgG antibody through intravenous injection. On day 6, the mice were euthanized by $CO_2$ asphyxiation. Matrigel plugs were removed, weighed and photographed. To measure hemoglobin levels, the Matrigel plug was lysed with a lysis buffer (1% SDS, 0.5% Triton in PBS) overnight at 4° C. The hemoglobin contents of the plugs were quantitated using Drabkin's reagent (Sigma). The concentrations of hemoglobin in the plugs were determined using a standard curve of bovine hemoglobin (Sigma). Hemoglobin contents were indicated as micrograms hemoglobin per gram Matrigel. Mean+SD were calculated using the Student's unpaired t test; $p<0.05$ was considered as statistically significant.

(iii) Prostate PC3 Tumor Metastasis Assay Using an Intrasplenic Implantation Model Mice were anesthetized with Avertin (0.2 ml/10 g) and shaved on the left flank. They were then placed at the right lateral decubitus position and scrubbed with 75% alcohol at the left flank. The skin at the abdominal wall was incised longitudinally (parallel to the spine) for 1 cm. The spleen was exteriorized and stabilized gently. A 30-gauge needle on an insulin syringe was inserted into the parenchyma of the spleen for 3-4 mm. 50 µl of a PC-3 cell suspension was injected slowly. A visible pale wheal indicates a successful injection. The needle was then retracted and a small cotton ball was placed to cover the injection site for 30 seconds to prevent bleeding and spillage of the cell suspension. The spleen was placed back into the peritoneum. The abdominal wall was closed with a 6-0 nylon suture, and the skin was closed with a 4-0 nylon suture.

After the implantation, the mice were randomly assigned to different treatment groups (Docetaxel group Docetaxel plus anti-IL6 antibody group, and PBS control group) and were treated with multiple doses of anti-IL6 antibody (20 mg/kg each time, twice a week), Docetaxel (3 mg/kg each time, once per week) through the tail vein or by i.p injection. The body weights of those mice were measured twice a week.

All mice were then euthanized by $CO_2$ asphyxiation and body weights were determined. Primary tumors in the spleen and liver were excised, photographed, and weighed. Organ index was expressed as milligram organ per gram mouse. Mean+SD were calculated using Student's t-test. The survival assay was used Kaplan-Meier analysis. Paraffin-embedded or frozen section of tumor masses were prepared and stained by anti-CD31 and Ki-67 plus Hematoxylin staining for analysis.

(iv) Xenograft Human Pancreatic Tumor Model

Human pancreatic tumor cells BxPC-3 and MiaPaCa cells were re-suspended in PBS and injected subcutaneously (s.c.) ($5\times10^6$ cells, total volume 0.15 mL) into the right flank of mice. After 10 days, the mice were randomly assigned to different treatment groups (Antibody FB704, Oxaliplatin, FB704 plus Oxaliplatin, Gemcitabine, and PBS control groups) and treated with multiple doses of FB704 (20 mg/kg each time, twice a week) or Oxaliplatin (3 mg/kg each time, once a week), or Gemcitabine (80 mg/kg each time, twice per week) through the tail vein or by i.p. injection. Mice body weights and the tumor sizes were measured twice a week.

Tumor sizes were measured using a caliper, and the tumor volume was calculated by length×width×0.52. After the experiment, all mice were sacrificed, mice blood samples were collected and the tumor masses were removed and weighted. The differences in mean tumor volume and tumor weight were evaluated by Student's t-test. Paraffin-embedded or frozen section of tumor masses were prepared and stained by anti-CD31, Ki67 or TUNEL plus H&E staining for analysis.

Results (i) FB704 Inhibits in Vivo Angiogenesis in a Matrigel Assay

Figure 4:
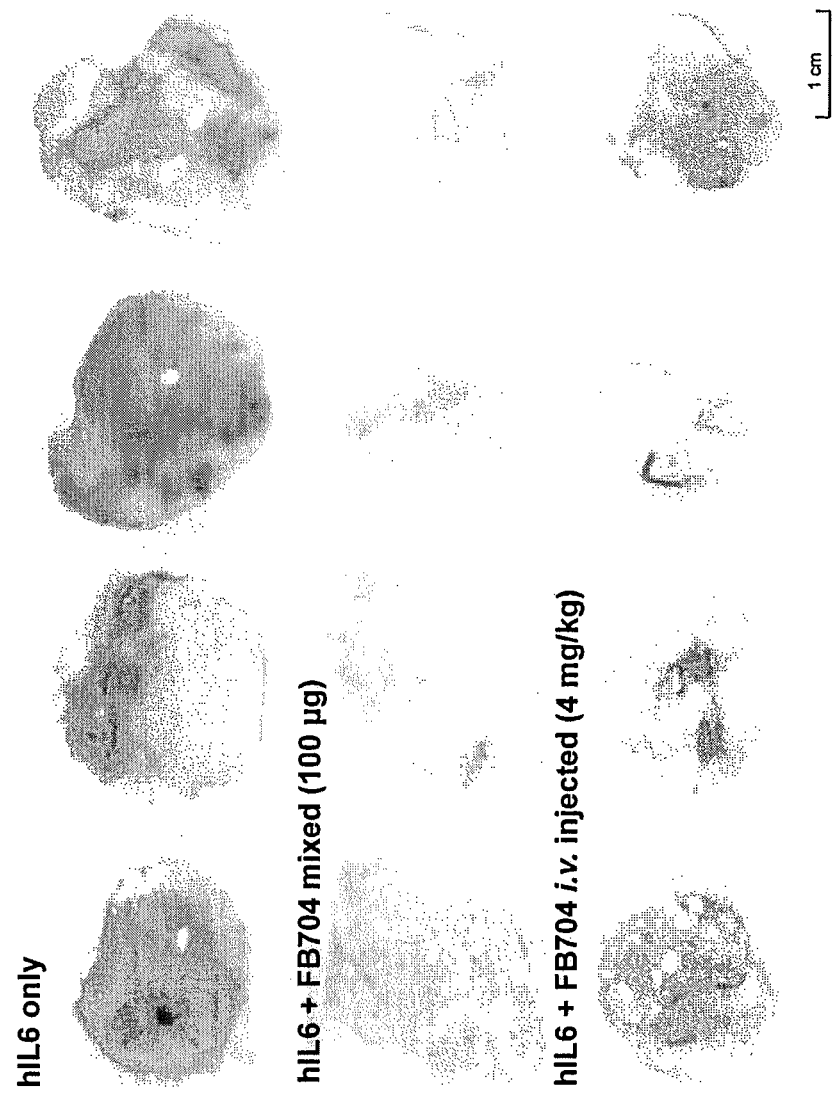
FIG. 4 is a diagram showing that antibody Ag1-4-6 (FB704) inhibited angiogenesis in vivo. hIL6 recombinant protein was added into matrigel and injected in two sites on the dorsal side of mice. Mice were treated with antibodies through i.v. injection or pre-mixture. (A) FB704 inhibited angiogenesis induced by IL6 as observed 6 days after treatment. (B) Treatment with antibody FB704 significantly changed the hemoglobin concentrations.
Figure 4:
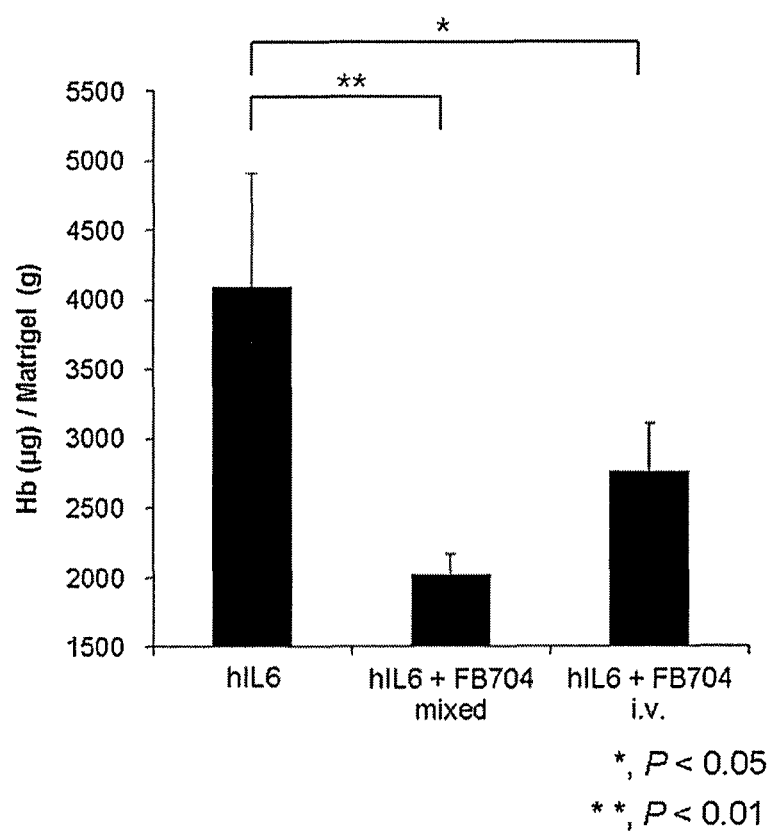

The anti-angiogenic ability of FB704 was examined in an in vivo matrigel model as described herein. Six days after the treatment, the mice were scarified mice and hemoglobin concentrations were measured. There was an observable difference in color and vessel density in excised matrigel plugs of FB704 treated groups (FIG. 4A), indicating the anti-angiogenic activity of the antibody. FB704 treatment also significantly reduced the hemoglobin concentrations as compared with hIL6. (FIG. 4B).

(ii) FB704 Inhibits Human Prostate Cancer Cell PC-3 Induced Cachexia and Metastasis To verify the efficacy of FB704 on cancer induced cachexia and metastasis, mice were implanted with human prostate cancer PC-3 cell ($1.0 \times 10^6$ per mouse) by intrasplenic injection. On day 1, the mice were randomized into 4 groups (n=12-15). High (20 mg/kg) and low (5 mg/kg) dose of FB704, positive control Actemra (20 mg/kg) and PBS were administered via i.v. (intravenous) injection twice a week. On day 31 after PC-3 cell implantation, the total body weights of PBS treated mice were decreased by approximately 19%. In contrast, the total body weights of the high dose FB704 and Actemra treated groups remained stable, which is significant different as compared with the control groups (FIG. 5A; P<0.01).

Figure 5:
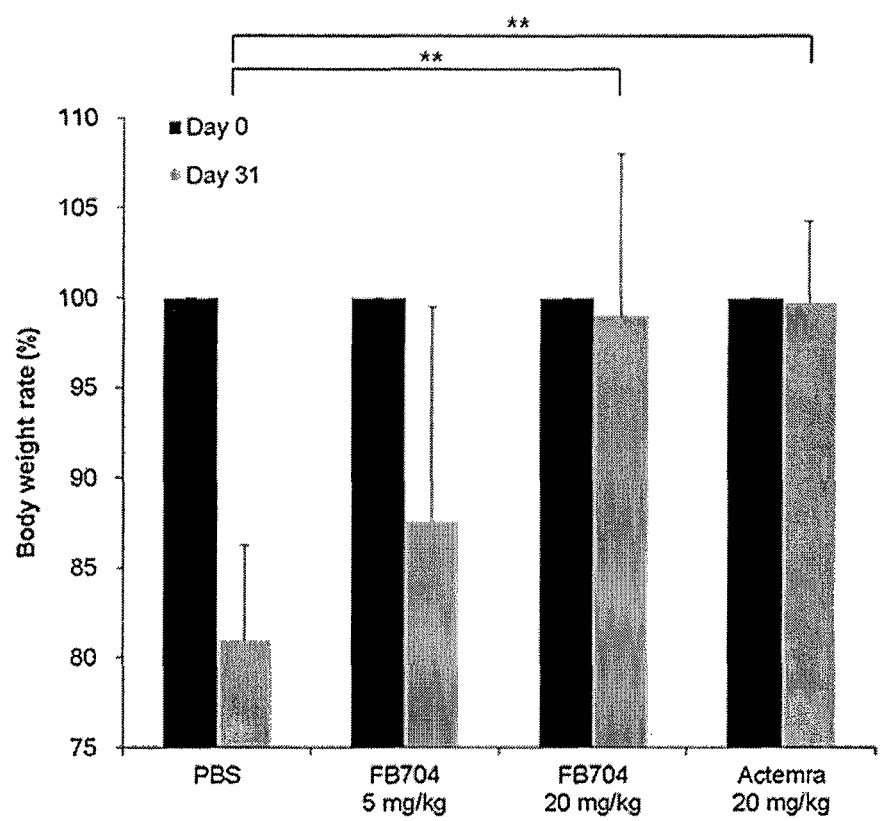
FIG. 5 is a diagram showing that antibody FB704 inhibited human prostate cancer cell PC-3 induced cachexia and metastasis. After tumor injection, mice body weights were measured on day 31. (A) The body weights of PBS-treated mice was decreased by approximately 19%. In contrast, high dose FB704- and Actemra-treated groups remained stable and showed significant different (P<0.01). (B) FB704 (n=15; P=0.00001) and Actemra (n=12; P=0.024) significantly prolonged symptom-free survival of PC3 tumor-bearing mice. FB704 showed significant better efficacy than Actemra (P=0.03). (C) Gross necropsy of PBS treated group showed severe enlargement and tumor cell infiltration in liver. However, FB704 treated group showed moderate tumor cell infiltration and nearly 50% normal hepatocyte in the left and middle lobes of liver. (D) Immunohistochemistry showed the vessel density was decreased after FB704 treated on tumor sections. (E) Semi-quantitative analysis of CD31 staining showed significantly decreased after FB704 treated (P<0.05). (F) Combination treatment of FB704 plus chemo-drug Docetaxel provided better overall survival rate.
Figure 5:
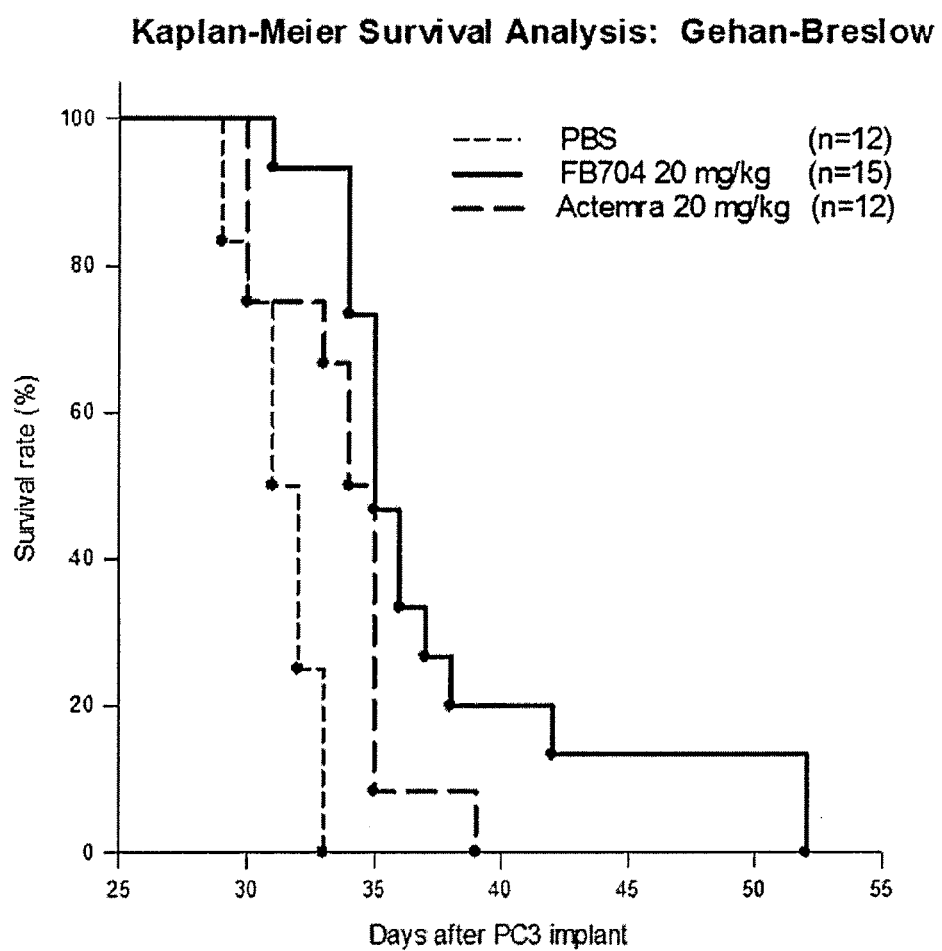
Figure 5:
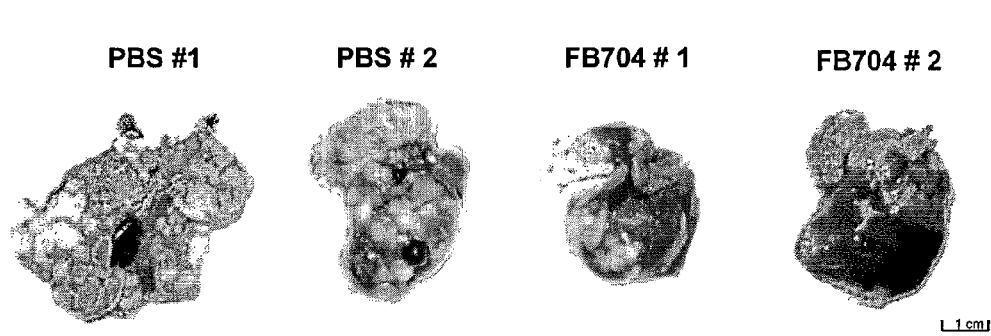
Figure 5:
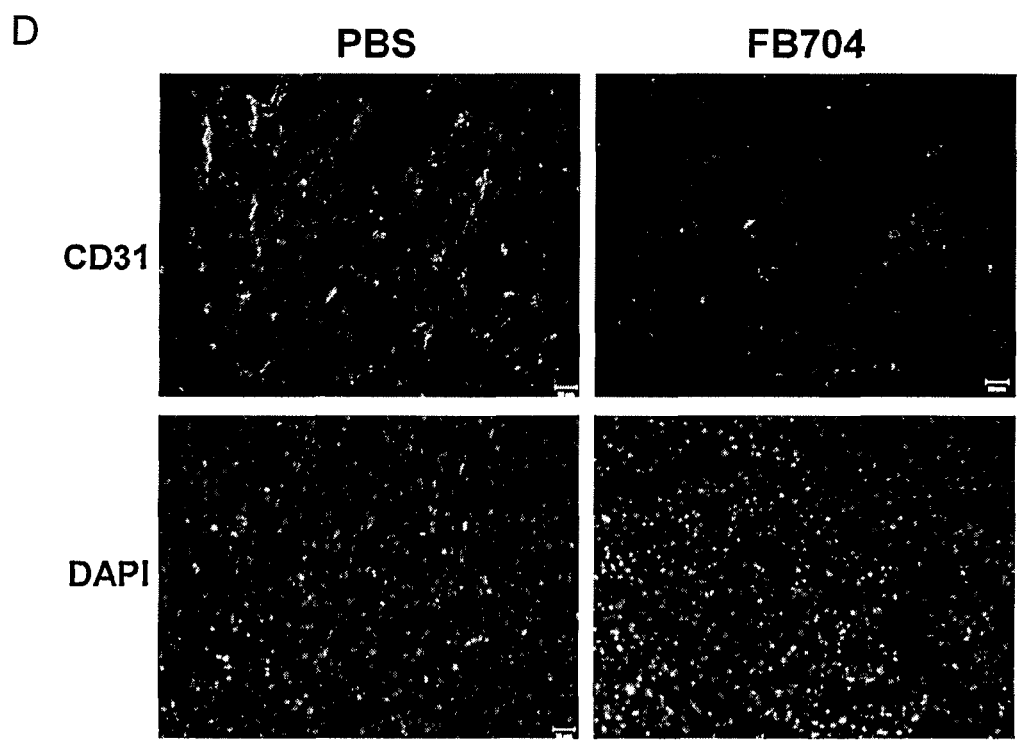
Figure 5:
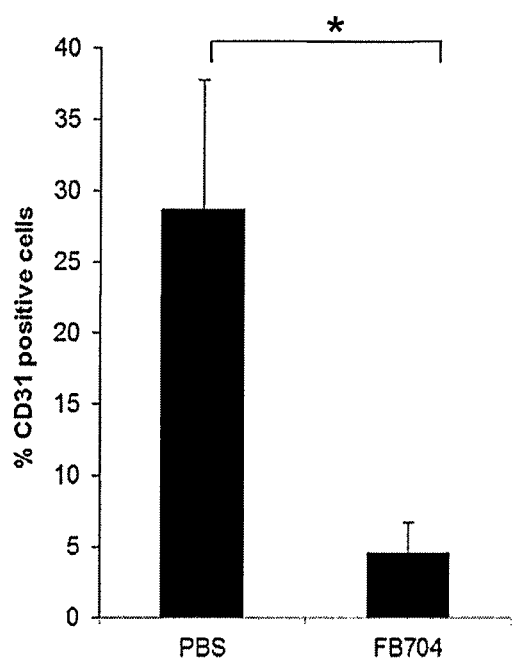
Figure 5:
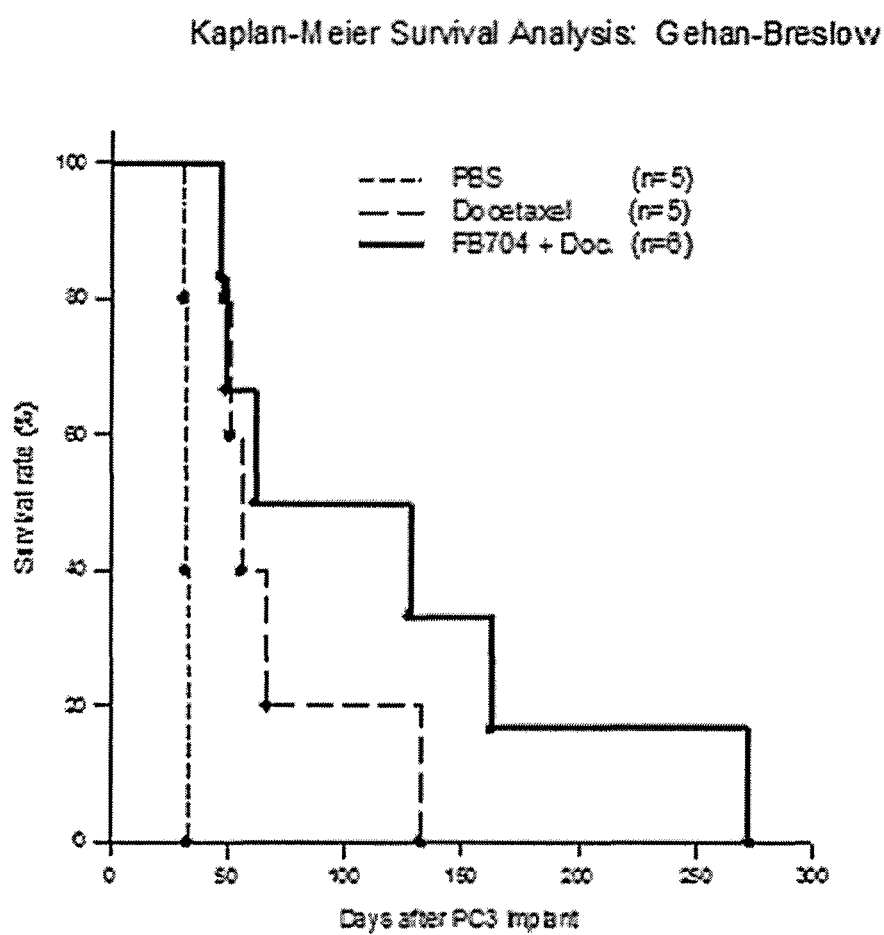

In addition, after a latency period of days, PC3 tumor-bearing mice developed hind leg paralysis or additional symptoms of disseminated tumor spread. Repetitive intra-vessel injections of FB704 (P=0.0001) and Actemra (P=0.024) significantly prolonged symptom-free survival of PC3 tumor-bearing mice, wherein FB704 showed significantly better efficacy than Actemra (P=0.03) (FIG. 5B). Gross necropsy of PBS treated group showed severe enlargement and tumor cell infiltration in liver. In contrast, FB704 treated group showed moderate tumor cell infiltration and more than 50% normal hepatocyte in the left and middle lobes of liver (FIG. 5C).

Angiogenesis also plays important rule in tumor metastasis. Immunohistochemistry was performed to verify the vessel density on tumor sections. Staining for CD31 (the marker for angiogenesis) showed that angiogenesis in the FB704 treated group was significantly decreased as compared with the PBS control group (FIGS. 5D and 5E).

Further, combined treatment of FB704 and chemo-drug Docetaxel provided better overall survival rates (FIG. 5F).

Figure 6:
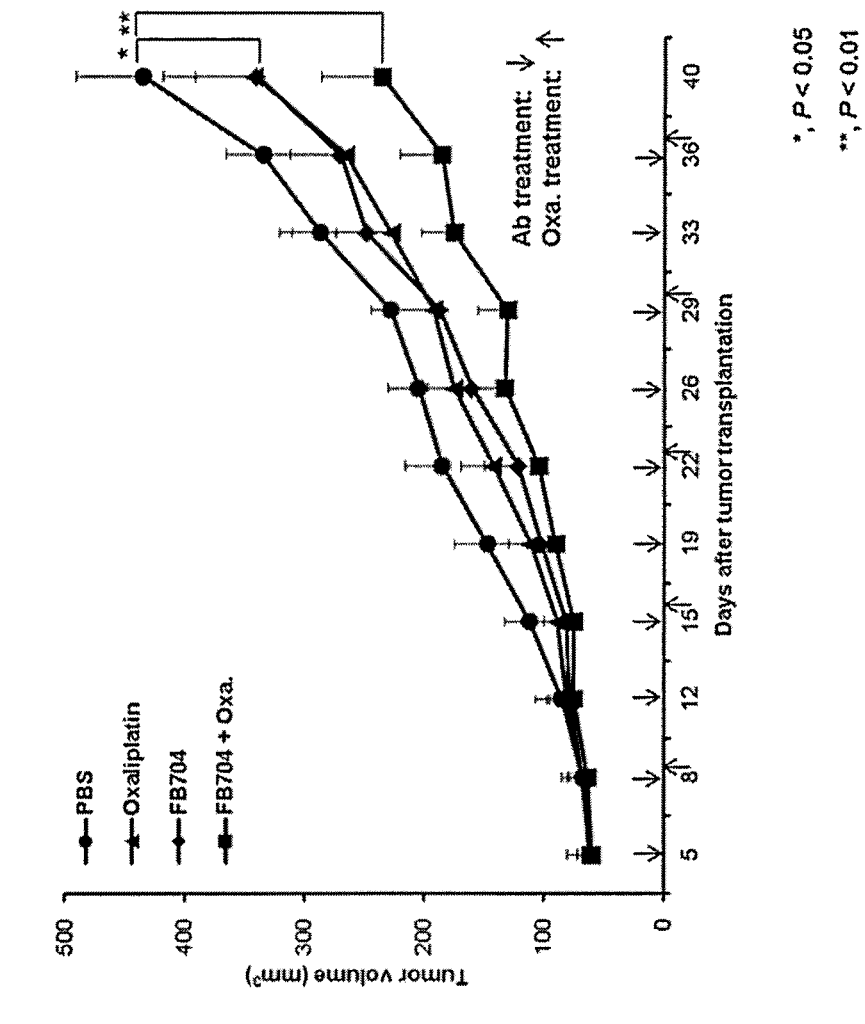
FIG. 6 is a diagram showing that antibody FB704 enhanced the anti-tumor activity of Oxaliplatin or Gemcitabine of pancreatic carcinoma xenograft. (A) Treatment of BxPC-3 tumor-bearing mice with 20 mg/kg of FB704 twice a week plus Oxaliplatin (3 mg/kg) once a week resulted in statistically significant tumor growth inhibition of 49% (P<0.01). (B) The mouse body weight had normally increased during the treatment. (C and D) The individual tumor masses were measured after the experiment and the tumor weights were significantly decreased after the treatments. (E) Tumor cell proliferation marker, Ki-67 was showed on different treatments of tumor section. (F) Ki-67 positive cell rate of PBS, Oxaliplatin, FB704 and FB704 plus Oxaliplatin treatment groups were showed 26%, 14%, 16% and 7.5% respectively. (G) Treatment of BxPC-3 tumor-bearing mice with 20 mg/kg of FB704 plus Gemcitabine (80 mg/kg) twice a week resulted in statistically significant tumor growth inhibition of 60% (P<0.01).
Figure 6:
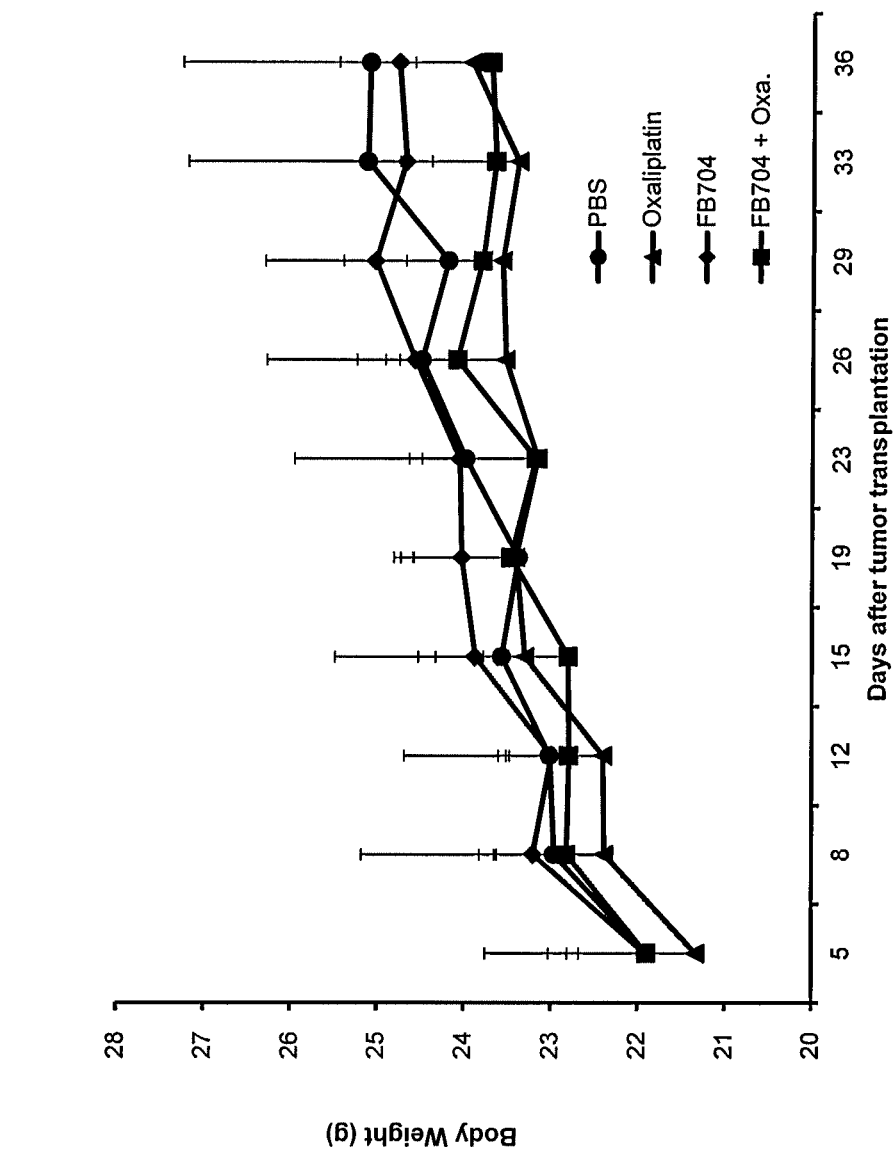
Figure 6:
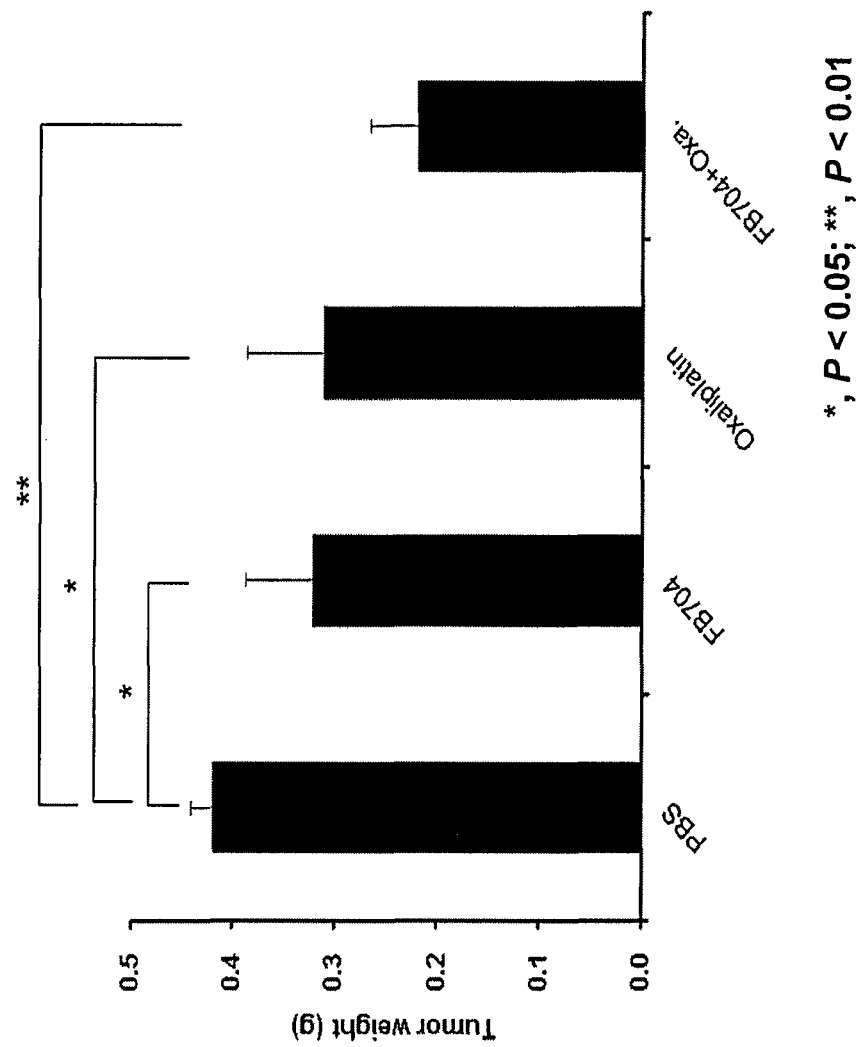
Figure 6:
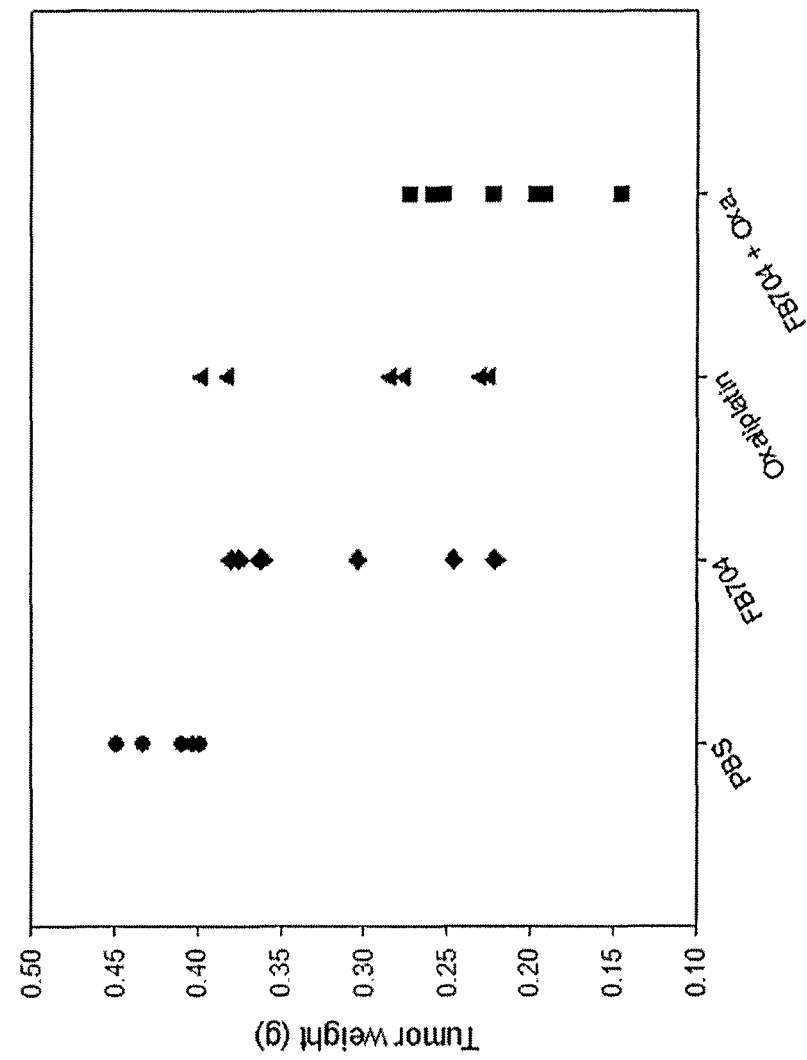
Figure 6:
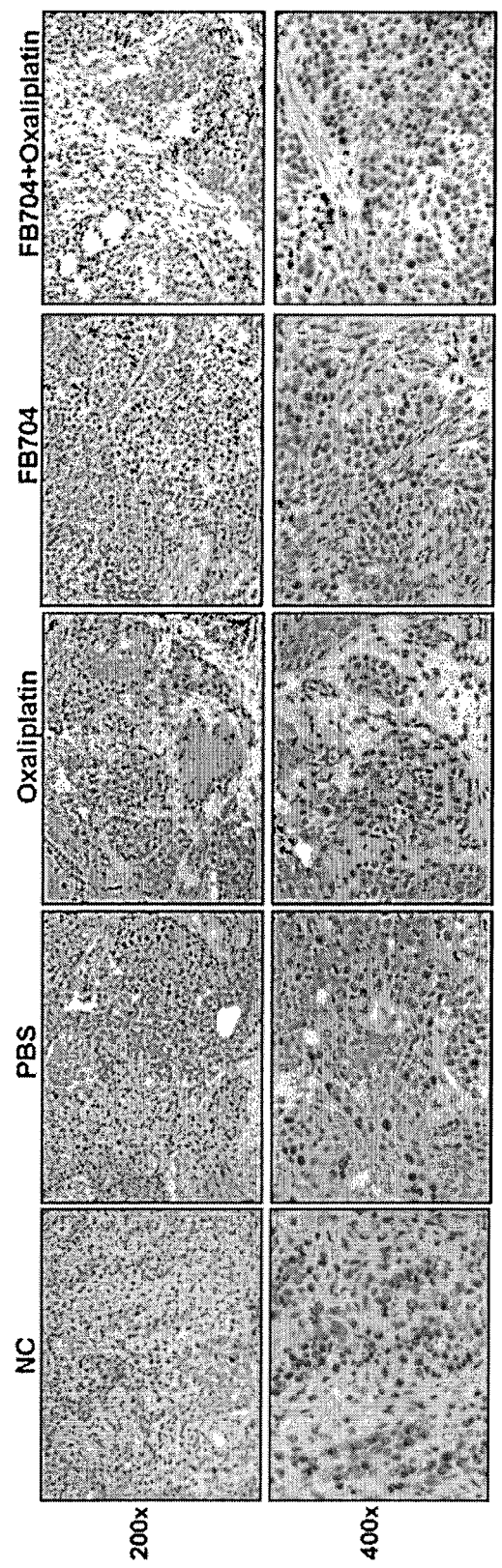
Figure 6:
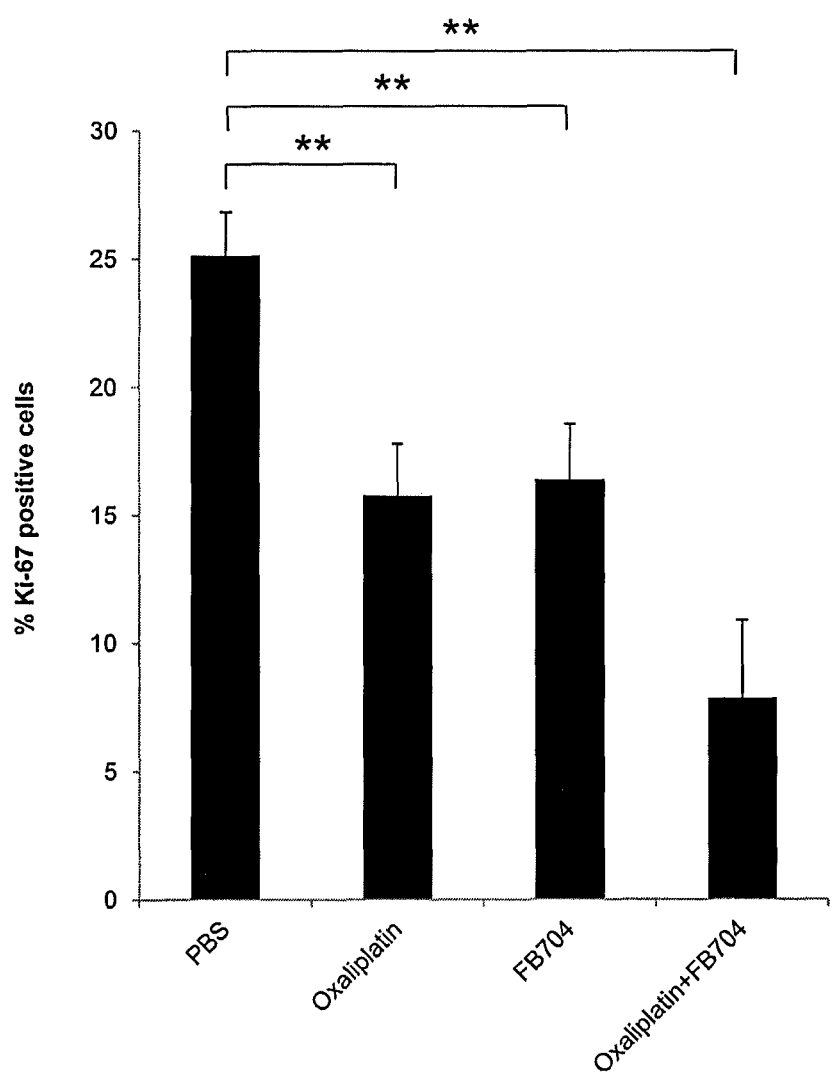
Figure 6:
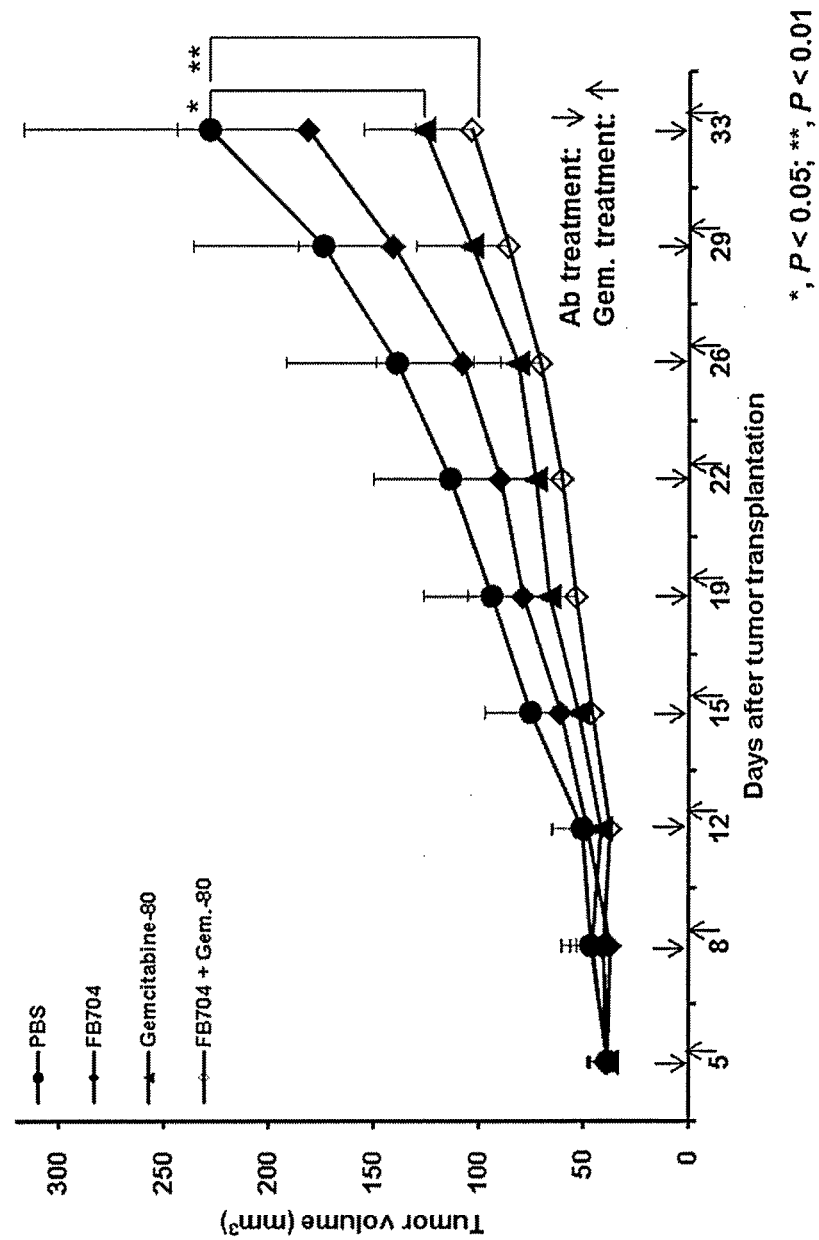

(iii) FB704 Enhances the Anti-Tumor Activity of Oxaliplatin or Gemcitabine in the Pancreatic Carcinoma Xenograft Model FB704 enhanced the anti-tumor activity of Oxaliplatin or Gemcitabine in a human pancreatic cancer model. Treatment of BxPC-3 tumor-bearing mice with 20 mg/kg of FB704 twice a week plus Oxaliplatin (3 mg/kg) once a week and Gemcitabin (80 mg/kg) twice a week resulted in statistically significant tumor growth inhibition of 49% and 60%, respectively (P<0.01) (FIGS. 6A and 6G). The mouse body weight had normally increased (FIG. 6B). The tumor mass weights were significantly reduced after the treatments (FIGS. 6C and 6D).

An antibody specific to Ki-67, which is a cell proliferation marker, was used to examine the tumor cell proliferation rates tumor tissues of each group. The percentages of Ki-67 positive cells in the PBS, Oxaliplatin, FB704 and FB704 plus Oxaliplatin treated groups were 26%, 14%, 16% and 7.5% respectively (FIGS. 6E and 6F), indicating that the combined treatments of FB704 and Oxaliplatin or Gemcitabine provided better inhibition of pancreatic tumor cell proliferation in vivo.

FB704 also showed synergic benefits with gemcitabine in a pancreatic cancer model. Treatment of BxPC-3 tumor-bearing mice with 20 mg/kg of FB704 and 80 mg/kg of gemcitabine twice a week resulted in statistically significant tumor growth inhibition (P<0.01) (FIG. 6G).

Example 4

Effectiveness of High Affinity Anti-IL6 Antibodies in Rheumatoid Arthritis Treatment In RA patient, elevated production of chemokine such as MCP-1 has been observed in joints, suggesting the involvement of chemokine in the pathogenesis of RA. Adhesion molecule, sICAM-1 also plays important roles in the infiltration of inflammatory cells into injured tissue. HUVEC naturally expressed sICAM-1 on cell surface. IL6 plus sIL6R treatment induced sICAM-1 expression.

(i) Anti-IL6 Antibodies Inhibited MCP-1 and sICAM-1 Production in HUVEC Cells

To examine the effectiveness of the anti-IL6 antibodies described herein in treating rheumatoid arthritis (RA), monocyte chemotactic protein-1 (MCP-1) and sICAM-1 secretion by Human Umbilical Vein Endothelial Cells (HUVECs) were measured after antibody treatment as follows. The HUVEC cells were plated in a 48-well plate at a density of $2 \times 10^5$ cells/ml. The cells were treated with a combination of recombinant human IL6, IL6 receptor-α (R&D systems) with or without anti-IL6 antibodies at various concentrations or the control IgG antibody at 37° C. for 24 h. Cell free culture supernatants were collected and analysis for MCP-1 and sICAM-1 by ELISA (RayBiotech)

Figure 2:
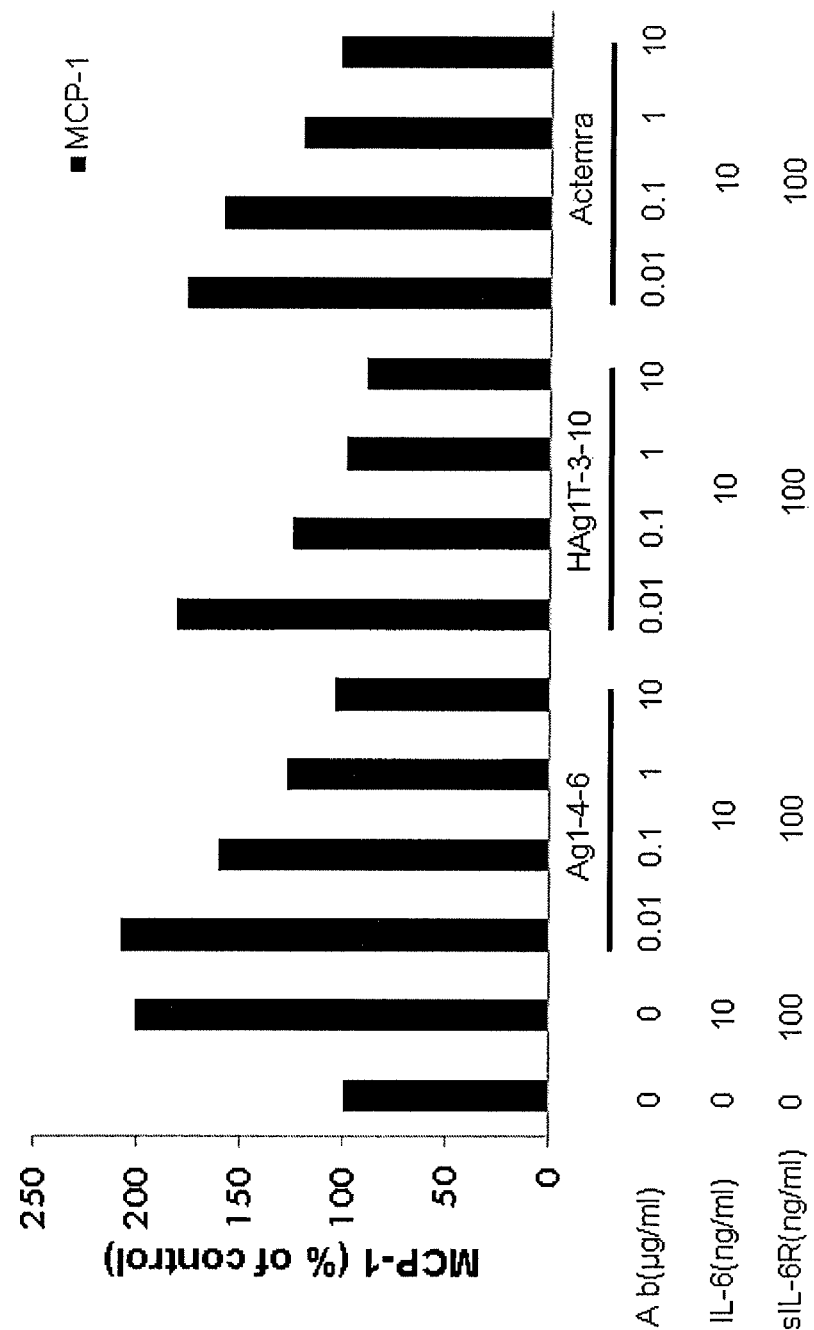
FIG. 2 is a diagram showing that anti-IL6 antibodies suppressed chemokine production in HUVEC cells. HUVECs were cultured with IL6, sIL6R, IL6 and sIL6R, or a combination of IL6, sIL6R, and an anti-IL6 antibody as indicated for 24 h. MCP-1 and sICAM-1 in the culture supernatant were measured by ELISA. (A) IL6+sIL6R induced MCP-1 secretion was inhibited by anti-IL6 antibodies Ag1-4-6 and Hag1T-3-10. (B) Antibodies Ag1-4-6 and Hag1T-3-10 inhibited production of sICAM-1 at a level greater than Actemra.
Figure 2:
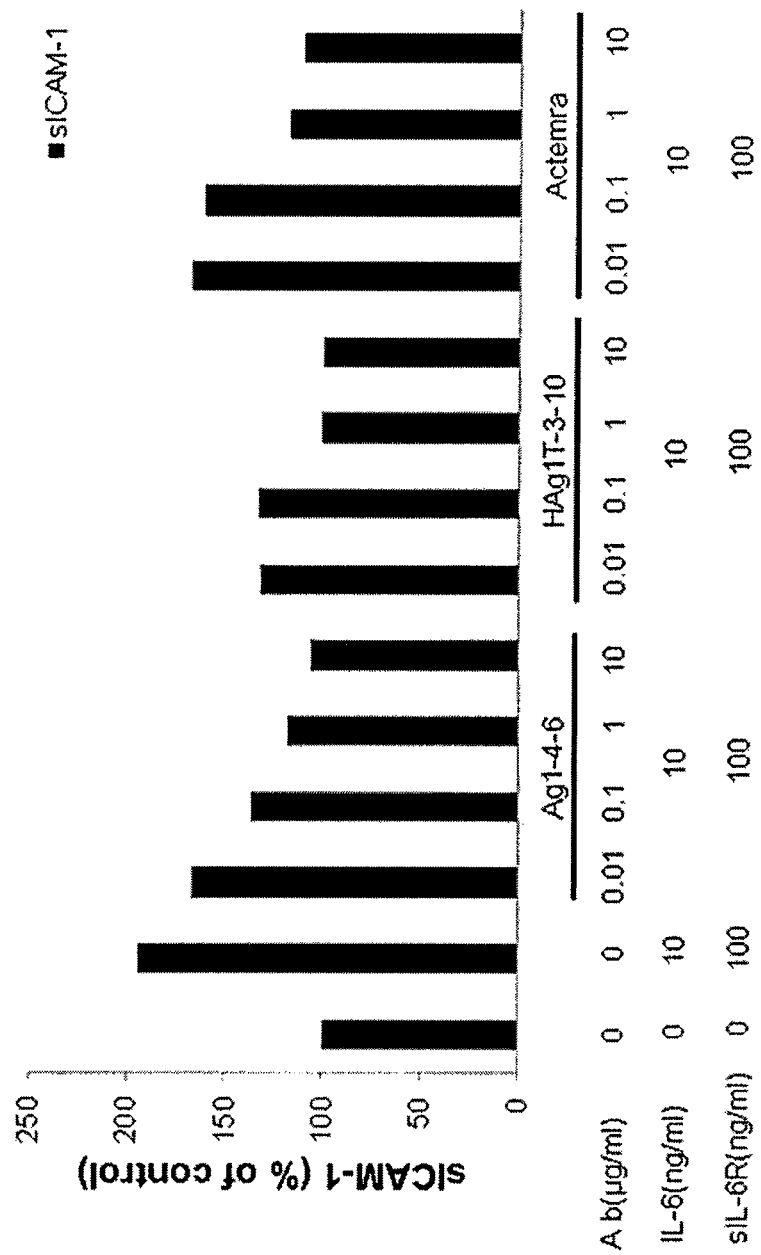

This in vitro assay indicated that IL6 plus sIL6Rα induced MCP-1 and sICAM-1 expression by HUVECs. Antibodies Ag1-4-6 and HAg1T-3-10 suppressed IL6 plus sIL6Rα induced MCP-1 (FIG. 2A) and sICAM-1 (FIG. 2B) in a dose dependent manner. The suppression efficacy was higher than Actemra.

(ii) Anti-IL6 Antibodies Inhibited MCP-1 Production in Both U937 Cells and Human Peripheral Blood Mononuclear Cell (PBMC)

MCP-1 is a small cytokine that belongs to the CC chemokine family, which recruits monocytes, memory T cells, and dendritic cells to the sites of inflammation. Among immune cells, monocytic cells are known to be the main producers of MCP-1. MCP-1 plays a major role on inflammatory and arthritis. Furthermore, IL6 was shown to induce MCP-1 in human monocytes. Therefore, the anti-IL6 antibodies described herein were tested for their effectiveness in suppressing MCP-1 expression in the promonocytic cell line U937 cells stimulated by IL6.

U937 ($2 \times 10^6$ cells/well) were cultured with IL6 (100 ng/ml) for 24 h in a 48 flat-bottomed culture plates (Corning, Corning, N.Y.) containing RPMI1640 in the presence of the anti-IL6 antibodies at different concentrations. The levels of MCP-1 in the supernatants were measured by MCP-1 ELISA kits (e Bioscience). All of the in vitro experiments were performed in triplicate.

Figure 7:
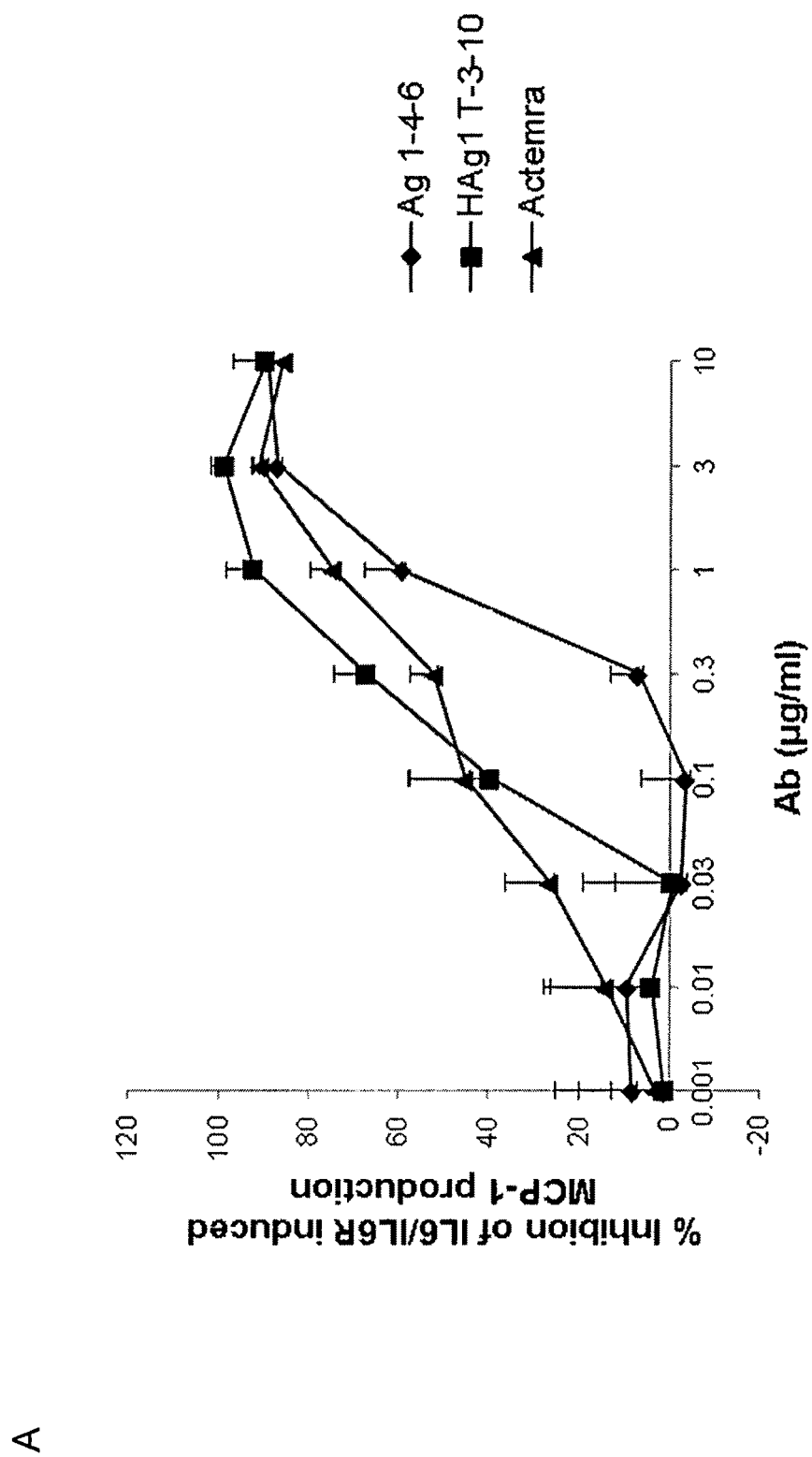
FIG. 7 is a diagram showing that exemplary anti-IL6 antibodies described herein suppressed MCP-1 production on U937 and human PBMC cells. (A) U937 cells were cultured with IL6 and treated by antibodies for 24 h. MCP-1 was measured by ELISA kit. Our antibodies show dose-dependently suppression of MCP-1 production (n=3). (B) PBMC cells were cultured with IL6 and treated by antibodies for 24 h. MCP-1 was measured by ELISA. Our antibodies showed dose-dependently suppression of MCP-1 production (n=5).
Figure 7:
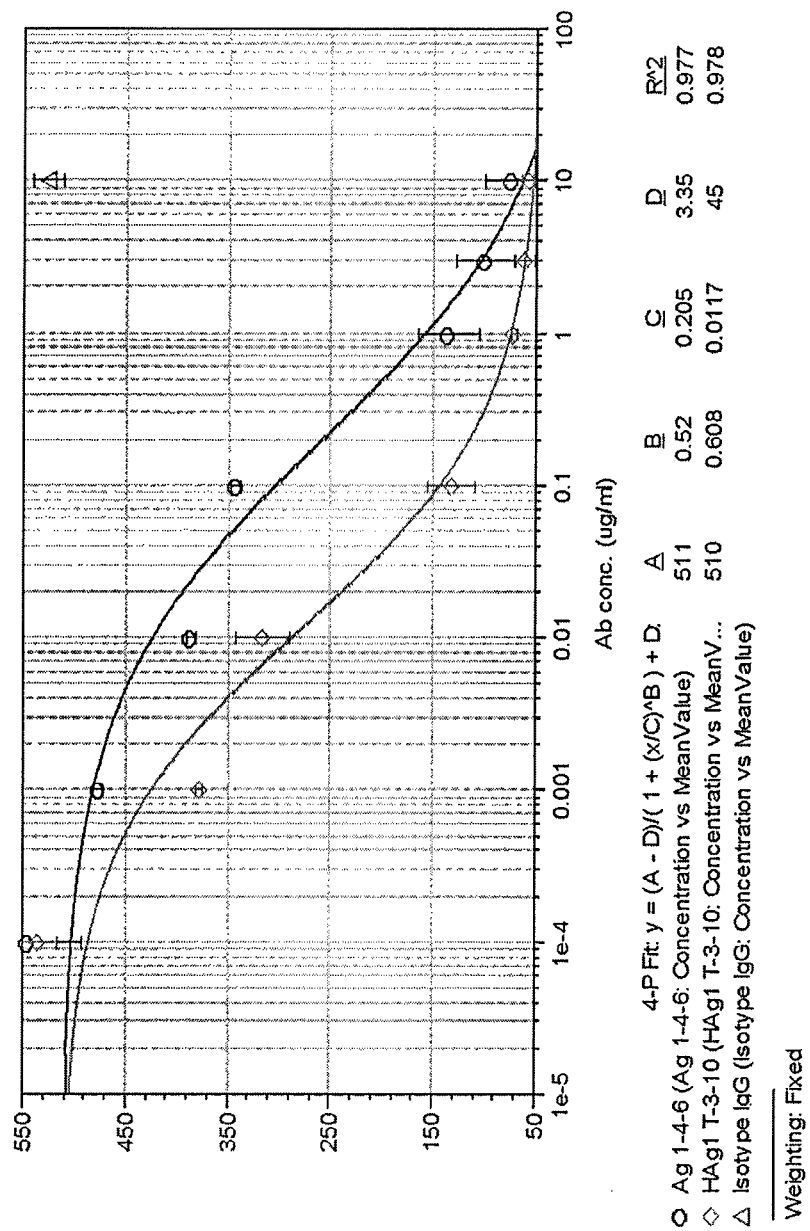

The production of MCP-1 from U937 cells was observed after IL6 stimulation and in a dose-dependent manner and anti-IL6 antibodies inhibited the MCP-1 production in U937 cells induced by IL6 (FIG. 7A).

Further, PBMCs were isolated from five healthy donors. The cells ($5 \times 10^5$ cells/250 µl/well) were cultured with IL6 (100 ng/ml) for 24 h in a 96-well U-bottomed culture plates (Corning, Corning, N.Y.) containing RPMI1640 in the presence of anti-IL6 antibodies at different concentrations. The levels of MCP-1 in the supernatant were measured by MCP-1 ELISA kits (e Bioscience).

The production of MCP-1 by PBMC cells was observed after IL6 stimulation. The presence of the antibodies Ag1-4-6 and HAg1T-3-10 inhibited MCP-1 production in a dose dependent manner, while a control isotype IgG1 did not show this inhibitory effect (FIG. 7B).

(iii) Anti-IL6 Antibodies Inhibited MCP-1 and VEGF Production in Synovial Fibroblasts from Rheumatoid Arthritis Patients Fresh synovial tissues were minced and digested in a solution of collagenase and DNase. Isolated fibroblasts were filtered through 70-mm nylon filters. The cells were grown on plastic cell culture dishes in 95% air/5% CO2 in RPMI 1640 (Life Technologies) that was supplemented with 20 mM HEPES and 10% heat-inactivated FBS, 2 mM glutamine, 100 U/ml penicillin, and 100 mg/ml streptomycin (pH adjusted to 7.6). More than 95% of the cells were fibroblasts, as characterized by immunofluorescence staining using an antibody specific for the fibroblast protein marker vimentin. Fibroblasts from passages four to nine were used for the experiments.

Fibroblast-like synnoviocyte derived from human RA patients as described above (RA-FLS cells) were cultured in a 6-well flat-bottomed culture plates (Corning, Corning, N.Y.; $2 \times 10^5$ cells/2 ml/well) for 2 days and were stimulated with both IL6 and sIL6R. Antibodies at various concentrations were added to the wells and incubated with the cells for 24 h. The MCP-1 levels were then measured by MCP-1 ELISA kits (e Bioscience).

Figure 8:
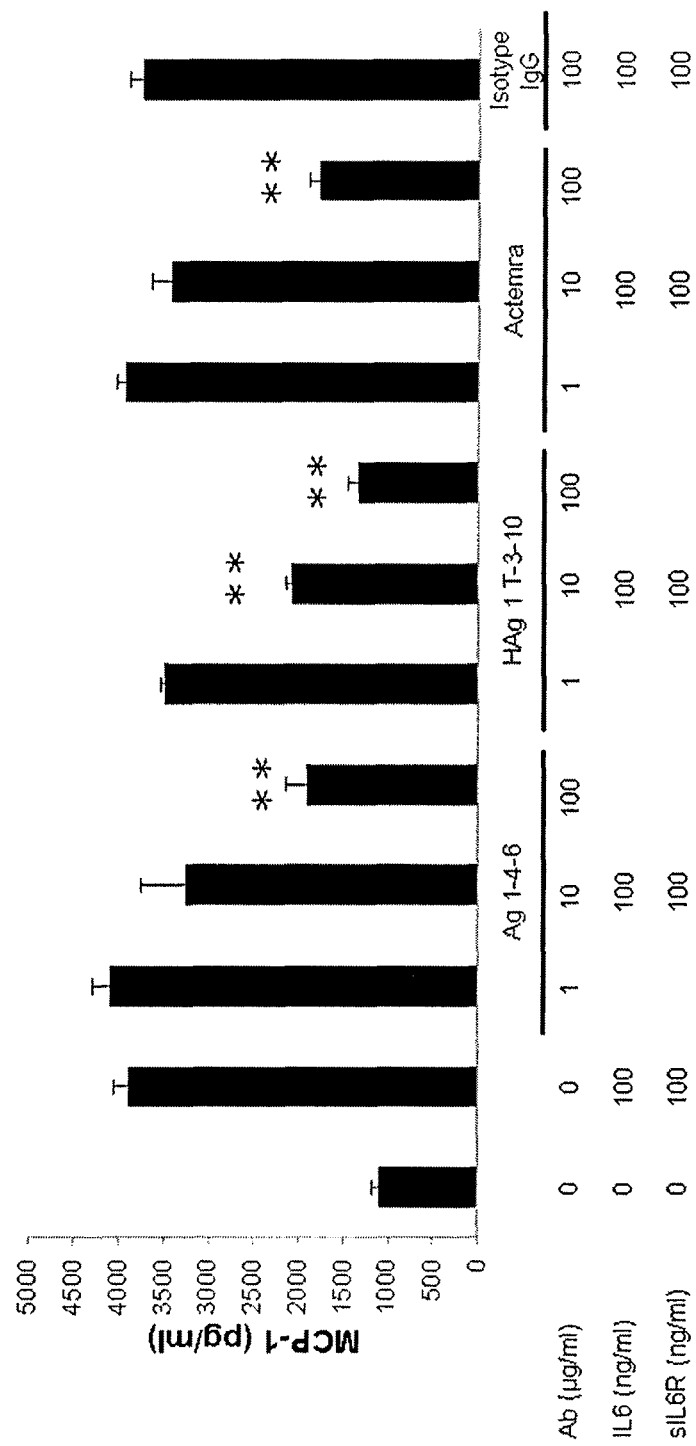
FIG. 8 is a diagram showing the Inhibition of MCP-1 production in RA-FLS by exemplary anti-IL6 antibodies described herein. (A) Commercial RA-FLS cells and (B) RA patients' FLS cells were cultured with IL6 plus sIL6R present or absent of antibodies for 24 h. Our antibodies show dose-dependently suppression of MCP-1 production (n=6).
Figure 8:
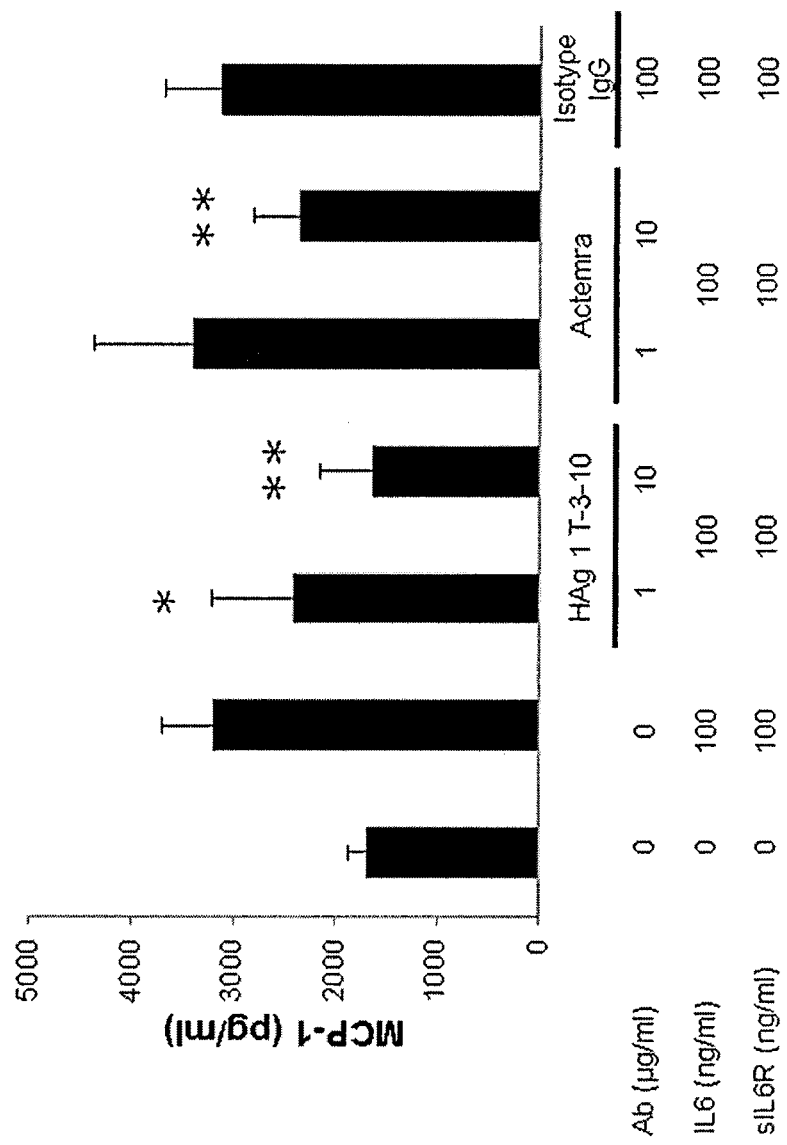

RA-FLS cells naturally express MCP-1 at low levels and pretreatment with IL6 and sIL6R could stimulate high level MCP-1 production. The anti-IL6 antibodies described herein showed significant inhibition of the MCP-1 production in commercially available RA-FLS cells (FIG. 8A) and the RA-FLS cells obtained from RA patients as described above (FIG. 8B).

Vascular endothelial growth factor (VEGF) plays an important role in the pathogenesis of RA. VEGF levels are significantly higher in synovial fluids from RA patients. It also induces vascular permeability and mediates inflammation. To examine the effect of anti-IL6 antibodies on VEGF production in RA-FLS cells, those cells were treated with the anti-IL6 antibodies described herein in the presence of IL6 (100 ng/ml), sIL6R (100 ng/ml), and IL1β (5 ng/ml) as follows.

The RA-FLS cells ($2 \times 10^4$ cells/500 ul/well) were cultured in a 48-well flat-bottomed culture plates (Corning, Corning, N.Y.) for 24 hours and then stimulated with both IL6 and sIL6R and IL-1β. Antibodies at various concentrations were added to the wells and incubated with the cells for 48 hours. The supernatants were collected and the levels of VEGF were measured by Human VEGF ELISA kit (PreproTech).

Figure 9:
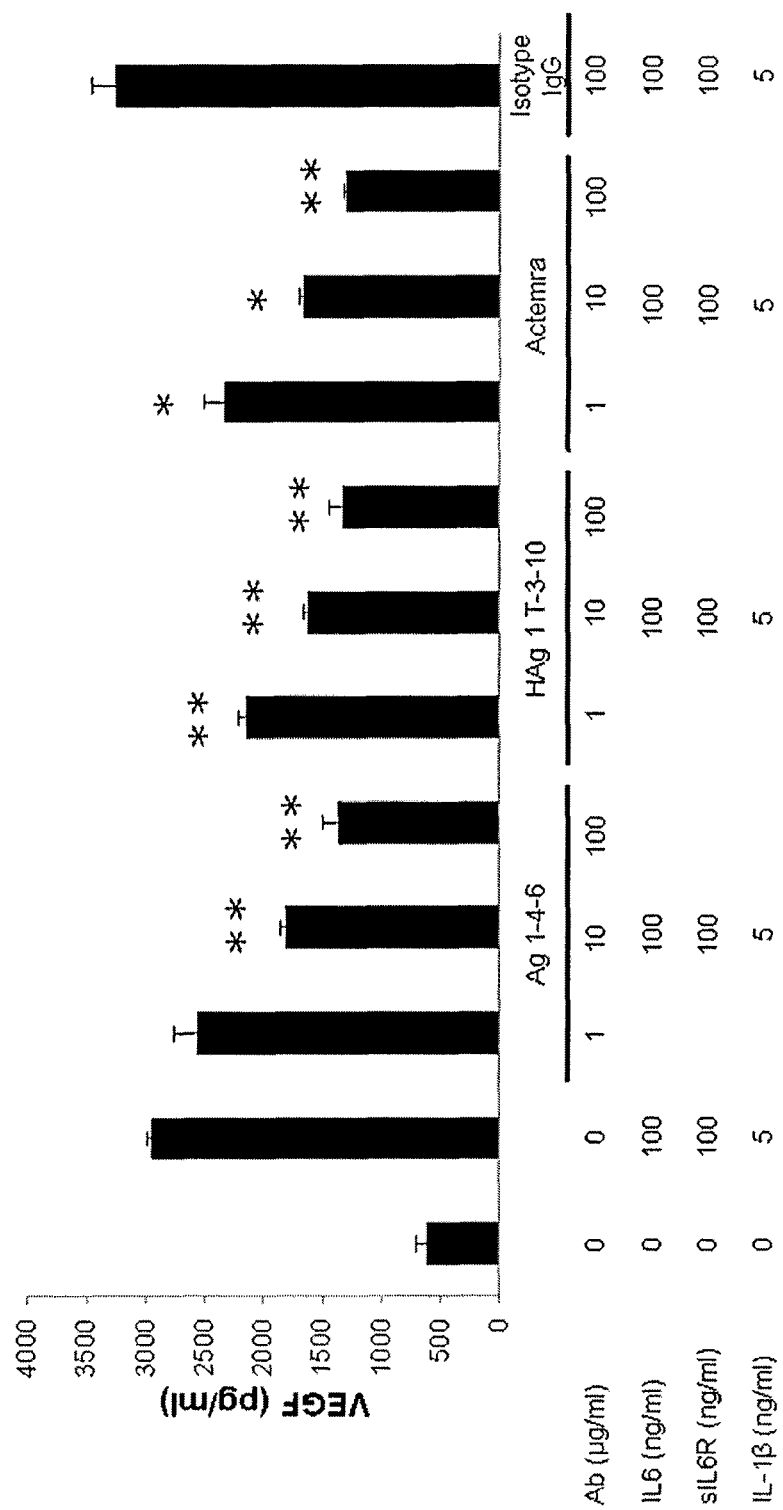
FIG. 9 is a diagram showing the inhibition of VEGF production in RA-FLS by exemplary anti-IL6 antibodies described herein. (A) Commercial RA-FLS cells and (B) RA patients' FLS cells were cultured with IL6, sIL6R and IL1β and treated with antibodies for 24 h. Our antibodies show dose-dependently suppression of VEGF production (n=6).
Figure 9:
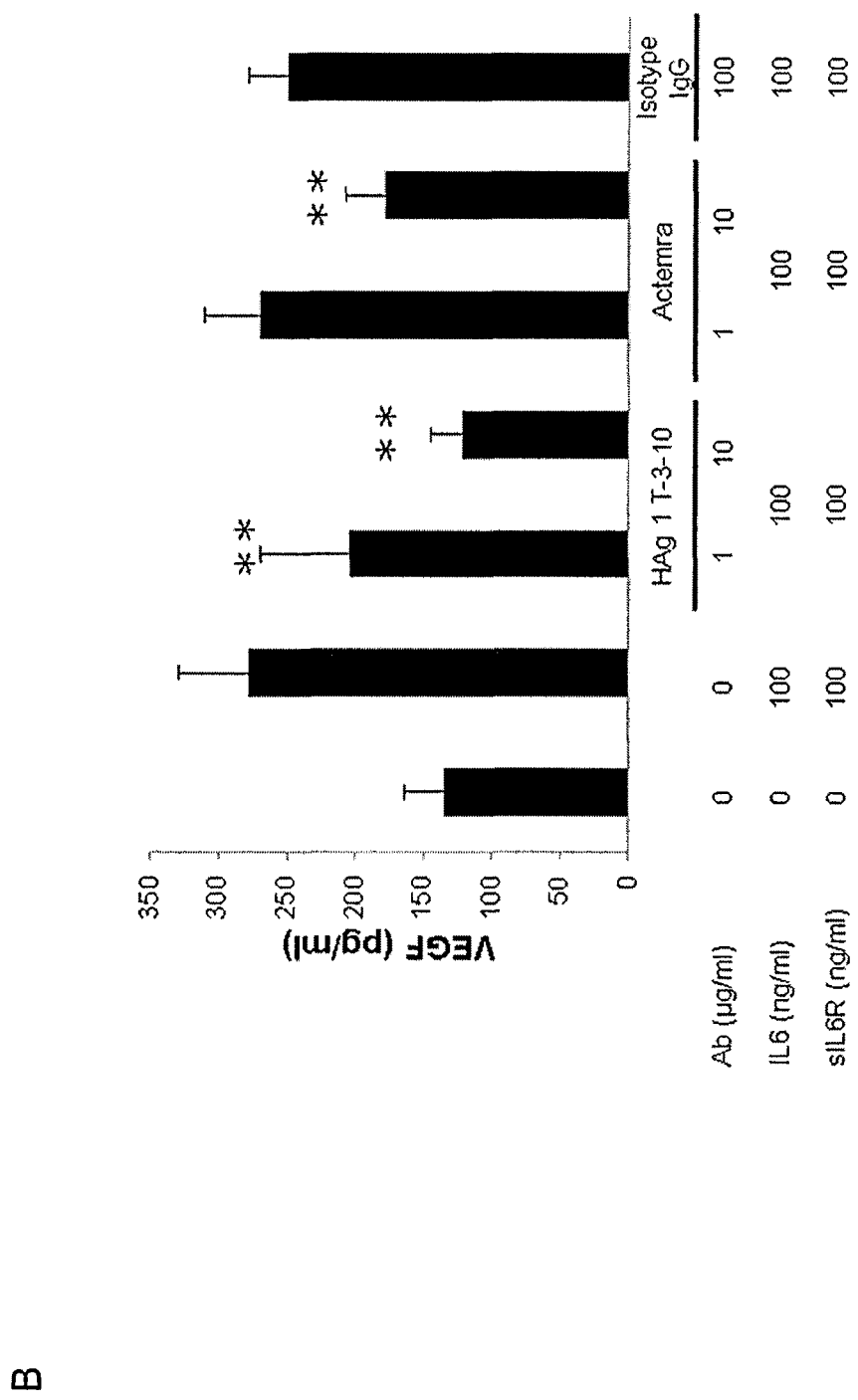

The VEGF in the culture supernatants of the RA-FLS cells stimulated with the combination of IL6, IL6R and IL1β was 3-5 fold higher than those in the supernatants from cells not stimulated by the cytokines. The Anti-IL6 antibodies significantly reduced Our the VEGF production in both commercially available RA-FLS cells (FIG. 9A) and the RA-FLS cells prepared from RA patients as described herein (FIG. 9B).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

---

What is claimed is:

1. An isolated antibody that binds to human interleukin 6 (IL6), comprising:
   (a) a heavy chain variable region ($V_H$), which comprises a heavy chain complementary determining region 1 (HC CDR1) of SEQ ID NO: 2, a heavy chain complementary determining region 2 (HC CDR2) of SEQ ID NO: 4, and a heavy chain complementary determining region 3 (HC CDR3) of SEQ ID NO: 6 or SEQ ID NO: 16; and
   (b) a light chain variable region ($V_L$), which comprises a light chain complementary determining region 1 (LC CDR1) of SEQ ID NO: 9, a light chain complementary determining region 2 (LC CDR2) of SEQ ID NO: 11, and a light chain complementary determining region 3 (LC CDR3) of SEQ ID NO: 13 or SEQ ID NO: 15.

2. The isolated antibody of claim 1, which comprises (i) a $V_H$ that comprises the HC CDR1 of SEQ ID NO: 2, the HC CDR2 of SEQ ID NO: 4, and the HC CDR3 of SEQ ID NO: 6; or (ii) a $V_H$ that comprises the HC CDR1 of SEQ ID NO: 2, the HC CDR2 of SEQ ID NO: 4, and the HC CDR3 of SEQ ID NO: 16.

3. The isolated antibody of claim 2, which comprises a $V_H$ that comprises the amino acid sequence of SEQ ID NO:17 or SEQ ID NO:18.

4. The isolated antibody of claim 2 or claim 3, which further comprises (i) a $V_L$ that comprises the LC CDR1 of SEQ ID NO: 9, the LC CDR2 of SEQ ID NO: 11, and the LC CDR3 of SEQ ID NO: 13; or (ii) a $V_L$ that comprises the LC CDR1 of SEQ ID NO: 9, the LC CDR2 of SEQ ID NO: 11, and the LC CDR3 of SEQ ID NO: 15.

5. The isolated antibody of claim 4, which comprises a $V_L$ that comprises the amino acid sequence of SEQ ID NO:19 or SEQ ID NO:20.

6. The isolated antibody of claim 1, which is selected from the group consisting of:
   (i) an antibody comprising a $V_H$ that comprises the HC CDR1 of SEQ ID NO: 2, the HC CDR2 of SEQ ID NO: 4, and the HC CDR3 of SEQ ID NO: 6; and a $V_L$ that comprises the LC CDR1 of SEQ ID NO: 9, the LC CDR2 of SEQ ID NO: 11, and the CDR3 of SEQ ID NO: 13;
   (ii) an antibody comprising a $V_H$ that comprises the HC CDR1 of SEQ ID NO: 2, the HC CDR2 of SEQ ID NO: 4, and the HC CDR3 of SEQ ID NO: 16, and a $V_L$ that comprises the LC CDR1 of SEQ ID NO: 9, the LC CDR2 of SEQ ID NO: 11, and the CDR3 of SEQ ID NO: 13;
   (iii) an antibody comprising a $V_H$ that comprises the HC CDR1 of SEQ ID NO: 2, the HC CDR2 of SEQ ID NO: 4, and the HC CDR3 of SEQ ID NO: 6, and a $V_L$ that comprises the LC CDR1 of SEQ ID NO: 9, the LC CDR2 of SEQ ID NO: 11, and the CDR3 of SEQ ID NO: 15; and
   (iv) an antibody comprising a $V_H$ that comprises the HC CDR1 of SEQ ID NO: 2, the HC CDR2 of SEQ ID NO: 4, and the HC CDR3 of SEQ ID NO: 16, and a $V_L$ that comprises the LC CDR1 of SEQ ID NO: 9, the LC CDR2 of SEQ ID NO: 11, and the CDR3 of SEQ ID NO: 15.

7. The isolated antibody of claim 6, which is selected from the group consisting of:
   (i) an antibody comprising a $V_H$ that comprises the amino acid sequence of SEQ ID NO: 17, and a $V_L$ that comprises the amino acid sequence of SEQ ID NO:19;
   (ii) an antibody comprising a $V_H$ that comprises the amino acid sequence of SEQ ID NO: 17, and a $V_L$ that comprises the amino acid sequence of SEQ ID NO:20; and
   (iii) an antibody comprising a $V_H$ that comprises the amino acid sequence of SEQ ID NO: 18, and a $V_L$ that comprises the amino acid sequence of SEQ ID NO:19; and
   (iv) an antibody comprising a $V_H$ that comprises the amino acid sequence of SEQ ID NO: 18, and a $V_L$ that comprises the amino acid sequence of SEQ ID NO:20.

8. The isolated antibody of claim 1, wherein the antibody is a full-length antibody or an antigen-binding fragment thereof.

9. The isolated antibody of claim 8, wherein the antigen-binding fragment thereof is Fab or (Fab')$_2$.

10. The isolated antibody of claim 1, wherein the antibody is a single chain antibody.

11. The isolated antibody of claim 1, wherein the antibody is a humanized antibody or a human antibody.

12. A composition comprising an antibody of claim 1 and a carrier.

13. A composition comprising an antibody of claim 1 and an anti-cancer agent or a disease modifying antirheumatic drug (DMARD).

14. The composition of claim 13, wherein the anti-cancer agent is selected from the group consisting of docetaxel, oxaliplatin, and gemcitabine.

15. The composition of claim 13, wherein the DMARDs is selected from the group consisting of methotrexate, azathioprine, chloroquine hydroxychloroquine, cyclosporin A, and sulfasalazine.

\* \* \* \* \*